(12) United States Patent
Sherburne

(10) Patent No.: US 12,213,900 B2
(45) Date of Patent: Feb. 4, 2025

(54) RADIAL EXPANSION AND CONTRACTION FEATURES OF MEDICAL DEVICES

(71) Applicant: ELEMENTAL PORTFOLIO, LLC, Saratoga, CA (US)

(72) Inventor: Paul Sherburne, St. Louis Park, MN (US)

(73) Assignee: Elemental Portfolio, LLC, Saratoga, CA (US)

( * ) Notice: Subject to any disclaimer, the term of this patent is extended or adjusted under 35 U.S.C. 154(b) by 713 days.

(21) Appl. No.: 16/817,573

(22) Filed: Mar. 12, 2020

(65) Prior Publication Data
US 2020/0214859 A1 Jul. 9, 2020

Related U.S. Application Data

(62) Division of application No. 15/159,801, filed on May 20, 2016, now Pat. No. 10,603,195.
(Continued)

(51) Int. Cl.
*A61F 2/95* (2013.01)
*A61B 17/00* (2006.01)
(Continued)

(52) U.S. Cl.
CPC ............. *A61F 2/92* (2013.01); *A61B 17/00* (2013.01); *A61F 2/95* (2013.01); *A61M 29/00* (2013.01)

(58) Field of Classification Search
CPC . A61F 2/95–2/97; A61F 2/2427; A61F 2/243; A61F 2/2433; A61F 2/2439;
(Continued)

(56) References Cited

U.S. PATENT DOCUMENTS 4,601,713 A 7/1986 Fuqua
4,602,911 A 7/1986 Ahmadi et al.
(Continued)

FOREIGN PATENT DOCUMENTS

CN 101612436 B 9/2011
EP 2363099 A1 9/2011
WO WO2007/138608 12/2007

OTHER PUBLICATIONS

Binder et al., "Transcatheter Aortic Valve Replacement with a New Self-Expanding Transcatheter Heart Valve and Motorized Delivery System," *J Am Coll Cardiol Intv*, vol. 6, No. 3, pp. 301-307, 2013.

*Primary Examiner* — Kathleen S Holwerda
(74) *Attorney, Agent, or Firm* — Smyrski Patent Law PC

(57) ABSTRACT

This disclosure concerns medical devices, such as catheters and implantable devices, having radially adjustable features. More particularly, the catheters and implantable devices can radially expand and contract to perform various functions within the body. Expansion and contraction can be performed by a radially adjustable structure mounted on the medical device. For example, a medical device can include an body configured for in vivo introduction, a strip attached to the body and rolled into a ring such that layers of the strip radially overlap each other, and at least one motor actuatable by electrical energy to move the radially overlapping layers of the strip relative to one another and change a diameter of the ring and the body.

20 Claims, 23 Drawing Sheets

Related U.S. Application Data

(60) Provisional application No. 62/164,032, filed on May 20, 2015.

(51) Int. Cl.
*A61F 2/24* (2006.01)
*A61F 2/92* (2013.01)
*A61M 29/00* (2006.01)

(58) Field of Classification Search
CPC ....... A61B 17/00; A61M 29/00; A61M 25/10; A61M 25/104
See application file for complete search history.

(56) References Cited

U.S. PATENT DOCUMENTS

| | | |
|---|---|---|
| 4,722,335 A | 2/1988 | Vilasi |
| 4,738,666 A | 4/1988 | Fuqua |
| 4,917,085 A | 4/1990 | Smith |
| 5,112,347 A | 5/1992 | Taheri |
| 5,176,659 A | 1/1993 | Mancini et al. |
| 5,183,464 A | 2/1993 | Dubrul et al. |
| 5,256,150 A | 10/1993 | Quiachon et al. |
| 5,318,588 A | 6/1994 | Horzewski et al. |
| 5,389,073 A | 2/1995 | Imran |
| 5,419,312 A | 5/1995 | Arenberg et al. |
| 5,441,515 A | 8/1995 | Khosravi et al. |
| 5,441,516 A | 8/1995 | Wang et al. |
| 5,443,477 A | 8/1995 | Marin et al. |
| 5,456,667 A | 10/1995 | Ham et al. |
| 5,713,907 A | 2/1998 | Hogendijk et al. |
| 5,771,902 A | 6/1998 | Lee et al. |
| 5,776,181 A | 7/1998 | Lee et al. |
| 5,797,951 A | 8/1998 | Mueller |
| 5,855,565 A | 1/1999 | Bar-Cohen et al. |
| 5,910,145 A | 6/1999 | Fischell et al. |
| 5,957,929 A | 9/1999 | Brenneman |
| 5,972,029 A | 10/1999 | Fuisz |
| 5,997,508 A | 12/1999 | Lunn et al. |
| 6,004,328 A | 12/1999 | Solar |
| 6,048,307 A | 4/2000 | Grundl et al. |
| 6,053,873 A | 4/2000 | Govari et al. |
| 6,066,094 A | 5/2000 | Ben-Haim |
| 6,110,198 A | 8/2000 | Fogarty et al. |
| 6,120,534 A | 9/2000 | Ruiz |
| 6,139,573 A | 10/2000 | Sogard et al. |
| 6,190,357 B1 | 2/2001 | Ferrari et al. |
| 6,254,608 B1 | 7/2001 | Solar |
| 6,254,628 B1 | 7/2001 | Wallace et al. |
| 6,312,443 B1 | 11/2001 | Stone |
| 6,358,238 B1 | 3/2002 | Sherry |
| 6,402,760 B1 | 6/2002 | Fedida |
| 6,423,032 B2 | 7/2002 | Parodi |
| 6,470,892 B1 | 10/2002 | Forsell |
| 6,497,724 B1 | 12/2002 | Stevens et al. |
| 6,514,237 B1 | 2/2003 | Maseda |
| 6,547,801 B1 | 4/2003 | Dargent et al. |
| 6,558,396 B1 | 5/2003 | Inoue |
| 6,579,297 B2 | 6/2003 | Bicek et al. |
| 6,632,236 B2 | 10/2003 | Hogendijk |
| 6,650,920 B2 | 11/2003 | Schaldach et al. |
| 6,716,230 B2 | 4/2004 | Whitman |
| 6,733,525 B2 | 5/2004 | Yang et al. |
| 6,749,556 B2 | 6/2004 | Banik |
| 6,755,855 B2 | 6/2004 | Yurek et al. |
| 6,764,494 B2 | 7/2004 | Menz et al. |
| 6,835,173 B2 | 12/2004 | Couvillon, Jr. |
| 6,940,211 B2 | 9/2005 | Pelrine et al. |
| 6,951,555 B1 | 10/2005 | Suresh et al. |
| 6,969,395 B2 | 11/2005 | Eskuri |
| 7,022,131 B1 | 4/2006 | Derowe et al. |
| 7,037,319 B2 | 5/2006 | Weber |
| 7,063,671 B2 | 6/2006 | Couvillon, Jr. |
| 7,097,658 B2 | 8/2006 | Oktay |
| 7,235,098 B2 | 6/2007 | Palmaz |
| 7,236,821 B2 | 6/2007 | Cates et al. |
| 7,331,969 B1 | 2/2008 | Inganäs et al. |
| 7,338,509 B2 | 3/2008 | Mattison |
| 7,374,571 B2 | 5/2008 | Pease et al. |
| 7,390,294 B2 | 6/2008 | Hassler, Jr. |
| 7,507,252 B2 | 3/2009 | Lashinski et al. |
| 7,556,646 B2 | 7/2009 | Yang et al. |
| 7,695,512 B2 | 4/2010 | Lashinski et al. |
| 7,699,864 B2 | 4/2010 | Kick et al. |
| 7,722,662 B2 | 5/2010 | Steinke et al. |
| 7,824,443 B2 | 11/2010 | Salahieh et al. |
| 7,892,203 B2 | 2/2011 | Lenker et al. |
| 7,935,141 B2 | 5/2011 | Randall et al. |
| 7,947,071 B2 | 5/2011 | Schmid et al. |
| 7,951,186 B2 | 5/2011 | Eidenschink et al. |
| 7,972,346 B2 | 7/2011 | Bachmann et al. |
| 7,993,350 B2 | 8/2011 | Ventura et al. |
| 7,993,397 B2 | 8/2011 | Lashinski et al. |
| 8,043,206 B2 | 10/2011 | Birk |
| 8,092,481 B2 | 1/2012 | Nance et al. |
| 8,133,249 B2 | 3/2012 | Ortiz et al. |
| 8,182,418 B2 | 5/2012 | Durant et al. |
| 8,211,088 B2 | 7/2012 | DiCarlo et al. |
| 8,231,670 B2 | 7/2012 | Salahieh et al. |
| 8,298,161 B2 | 10/2012 | Vargas |
| 8,328,868 B2 | 12/2012 | Paul et al. |
| 8,388,628 B2 | 3/2013 | Eversull et al. |
| 8,398,693 B2 | 3/2013 | Weber et al. |
| 8,425,549 B2 | 4/2013 | Lenker et al. |
| 8,460,368 B2 | 6/2013 | Taylor et al. |
| 8,517,915 B2 | 8/2013 | Perron et al. |
| 8,540,762 B2 | 9/2013 | Schmid et al. |
| 8,647,378 B2 | 2/2014 | Mews et al. |
| 8,652,202 B2 | 2/2014 | Alon et al. |
| 8,673,001 B2 | 3/2014 | Cartledge et al. |
| 8,690,936 B2 | 4/2014 | Nguyen et al. |
| 8,758,372 B2 | 6/2014 | Cartledge et al. |
| 8,778,021 B2 | 7/2014 | Cartledge et al. |
| 8,790,387 B2 | 7/2014 | Nguyen et al. |
| 8,801,774 B2 | 8/2014 | Silverman |
| 8,808,356 B2 | 8/2014 | Braido et al. |
| 8,808,371 B2 | 8/2014 | Cartledge |
| 8,828,024 B2 | 9/2014 | Farritor et al. |
| 8,864,823 B2 | 10/2014 | Cartledge et al. |
| 8,945,210 B2 | 2/2015 | Cartledge et al. |
| 8,961,393 B2 | 2/2015 | Rion et al. |
| 9,017,253 B2 | 4/2015 | Guralnik et al. |
| 9,039,756 B2 | 5/2015 | White |
| 9,107,750 B2 | 8/2015 | Cartledge et al. |
| 9,149,277 B2 | 10/2015 | Rudakov et al. |
| 9,155,619 B2 | 10/2015 | Liu et al. |
| 9,161,834 B2 | 10/2015 | Taylor et al. |
| 9,247,942 B2 | 2/2016 | Rudakov et al. |
| 9,301,860 B2 | 4/2016 | White |
| 9,364,323 B2 | 6/2016 | White |
| 9,408,607 B2 | 8/2016 | Cartledge et al. |
| 9,566,178 B2 | 2/2017 | Cartledge et al. |
| 9,597,063 B2 | 3/2017 | Voss et al. |
| 9,700,442 B2 | 7/2017 | White |
| 9,770,243 B2 | 9/2017 | Wang et al. |
| 9,814,611 B2 | 11/2017 | Cartledge et al. |
| 9,827,093 B2 | 11/2017 | Cartledge et al. |
| 9,827,404 B2 | 11/2017 | Nance et al. |
| 10,045,847 B2 | 8/2018 | Liu et al. |
| 10,813,754 B2 | 10/2020 | He et al. |
| 2002/0032429 A1 | 3/2002 | Hjertman et al. |
| 2003/0094356 A1 | 5/2003 | Waldron |
| 2003/0135268 A1 | 7/2003 | Desai |
| 2003/0176786 A1 | 9/2003 | Maschke |
| 2004/0138733 A1* | 7/2004 | Weber .................. A61M 25/00 606/167 |
| 2005/0038497 A1 | 2/2005 | Neuendorf et al. |
| 2005/0085693 A1 | 4/2005 | Belson et al. |
| 2005/0149159 A1 | 7/2005 | Andreas et al. |
| 2005/0177223 A1* | 8/2005 | Palmaz .................. A61B 5/053 623/1.15 |
| 2005/0209627 A1 | 9/2005 | Kick et al. |
| 2005/0267407 A1 | 12/2005 | Goldman |
| 2005/0288551 A1 | 12/2005 | Callister et al. |

(56) References Cited

U.S. PATENT DOCUMENTS

| | | |
|---|---|---|
| 2006/0004439 A1* | 1/2006 | Spenser ............... A61F 2/2436 623/2.11 |
| 2006/0135981 A1 | 6/2006 | Lenker et al. |
| 2006/0212062 A1 | 9/2006 | Farascioni |
| 2006/0265041 A1* | 11/2006 | Sanati ...................... A61F 2/90 623/1.11 |
| 2007/0027519 A1* | 2/2007 | Ortiz ....................... A61F 2/966 623/1.11 |
| 2007/0044983 A1 | 3/2007 | Wuensch et al. |
| 2007/0100280 A1 | 5/2007 | Van Sloten |
| 2007/0213759 A1* | 9/2007 | Osborne ............... A61M 25/10 606/192 |
| 2007/0225797 A1 | 9/2007 | Krivoruhko |
| 2007/0265499 A1 | 11/2007 | Wood et al. |
| 2008/0004692 A1 | 1/2008 | Henson et al. |
| 2008/0045794 A1 | 2/2008 | Belson |
| 2008/0065136 A1 | 3/2008 | Young |
| 2009/0099638 A1 | 4/2009 | Grewe |
| 2009/0105794 A1 | 4/2009 | Ziarno et al. |
| 2009/0259093 A1 | 10/2009 | Bhat et al. |
| 2010/0036307 A1 | 2/2010 | Von Segesser |
| 2010/0081875 A1 | 4/2010 | Fowler et al. |
| 2010/0198160 A1 | 8/2010 | Voss |
| 2010/0211131 A1 | 8/2010 | Williams et al. |
| 2011/0098802 A1 | 4/2011 | Braido et al. |
| 2011/0270025 A1 | 11/2011 | Fridez et al. |
| 2012/0035437 A1 | 2/2012 | Ferren et al. |
| 2012/0059337 A1 | 3/2012 | Eilat |
| 2013/0041454 A1 | 2/2013 | Dobson et al. |
| 2013/0046373 A1 | 2/2013 | Cartledge et al. |
| 2013/0123757 A1 | 5/2013 | Crisostomo et al. |
| 2013/0253423 A1 | 9/2013 | Shin |
| 2014/0107489 A1 | 4/2014 | Fearnot et al. |
| 2014/0228814 A1 | 8/2014 | Zhou et al. |
| 2014/0277331 A1* | 9/2014 | Ngo ....................... A61F 2/0095 623/1.11 |
| 2014/0324094 A1* | 10/2014 | Weber ............... A61B 17/1204 606/198 |
| 2014/0343670 A1 | 11/2014 | Bakis |

\* cited by examiner

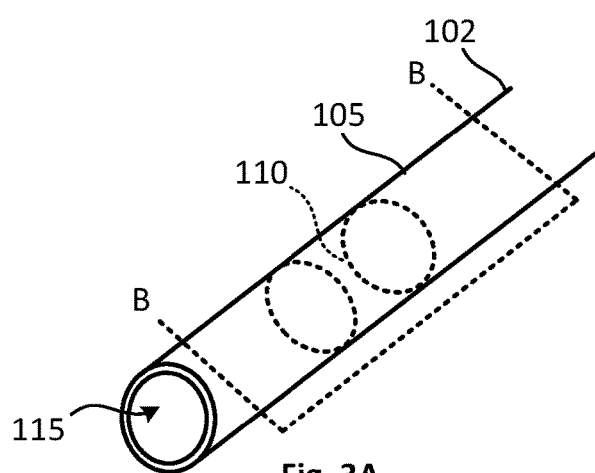
Fig. 3A
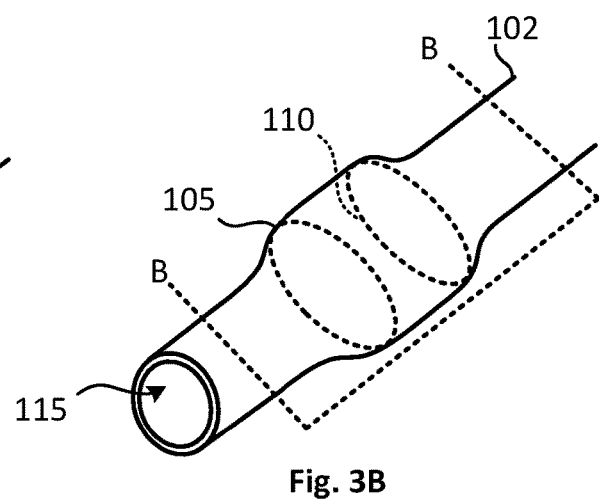
Fig. 3B
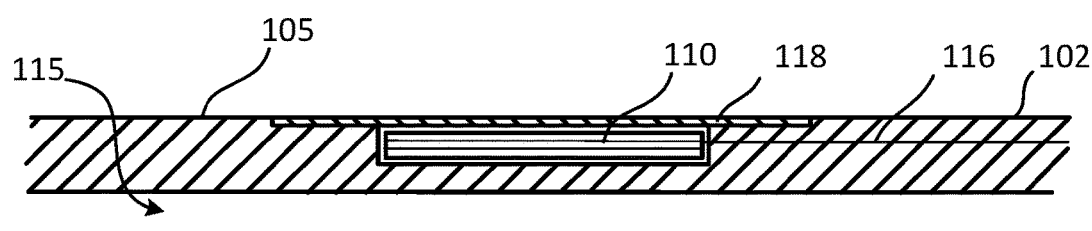
Fig. 3C
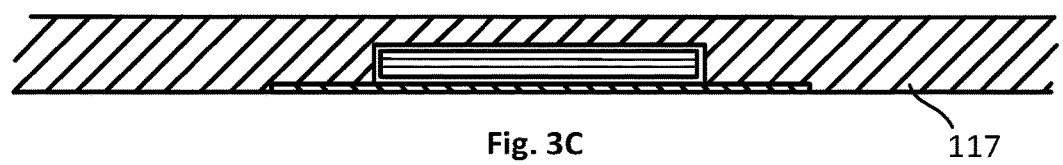
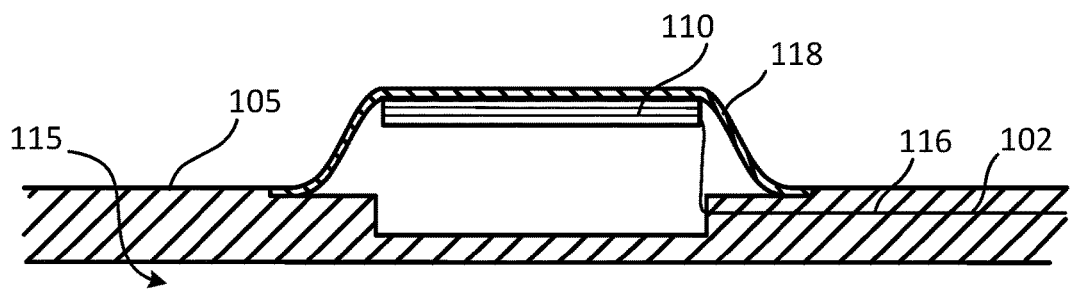
Fig. 3D
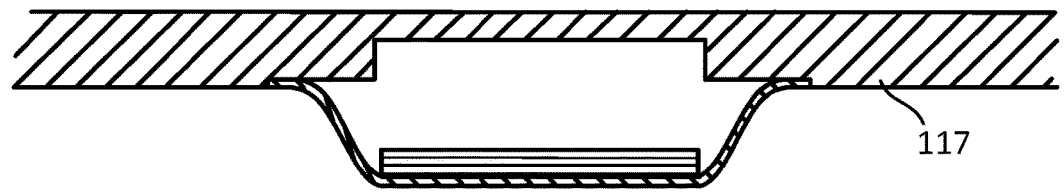

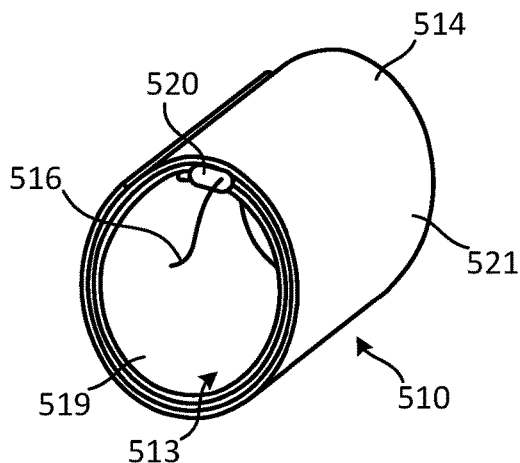
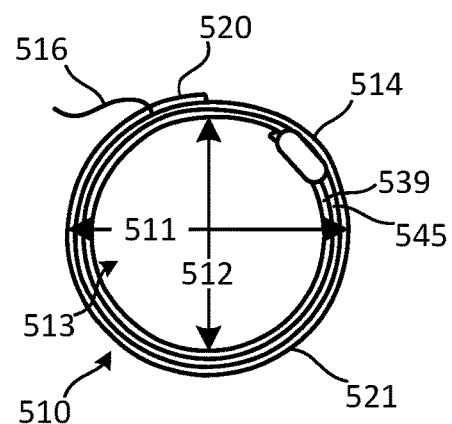
Fig. 7A
Fig. 7B
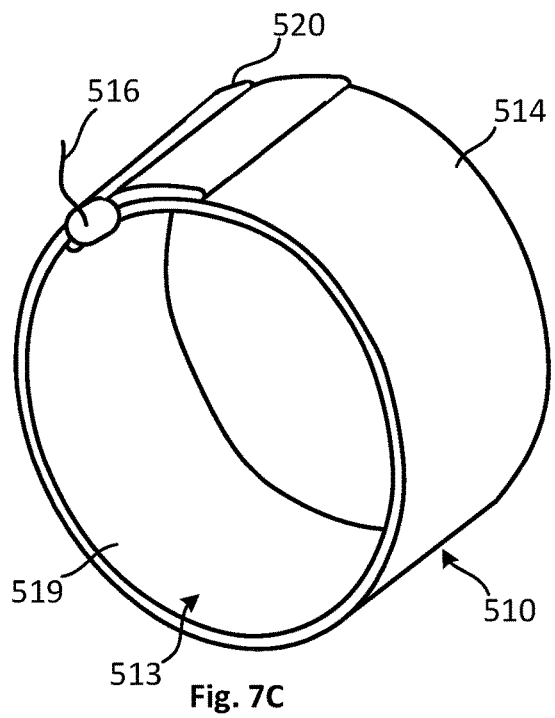
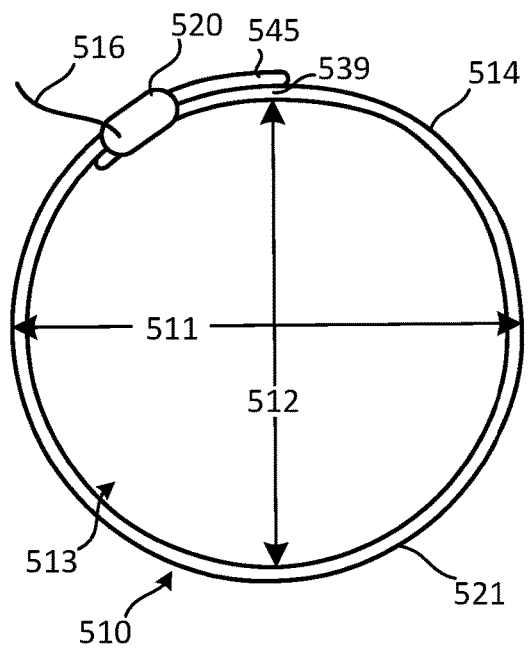
Fig. 7C
Fig. 7D

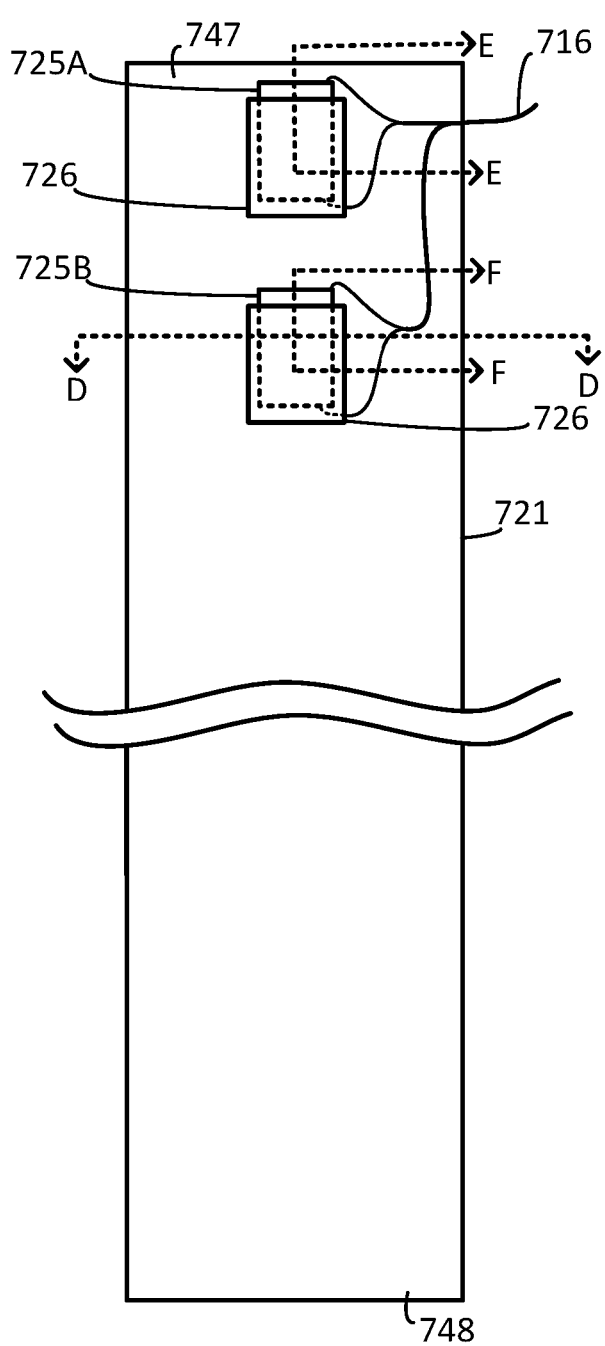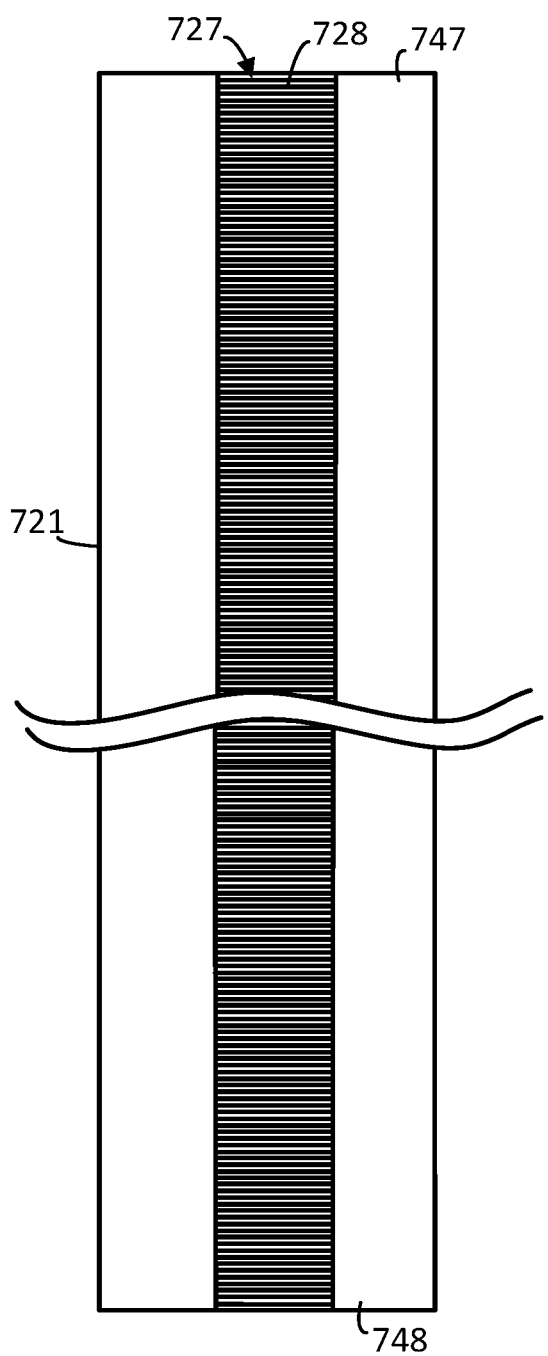
Fig. 9A    Fig. 9B
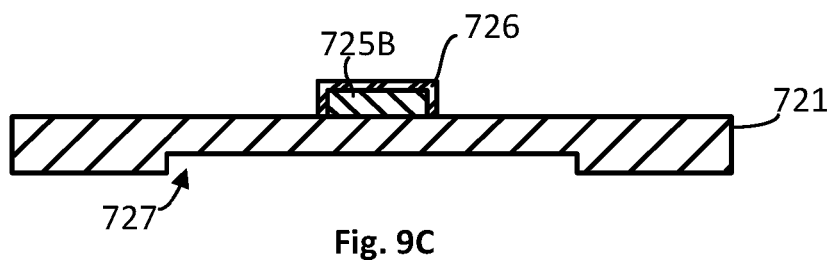
Fig. 9C

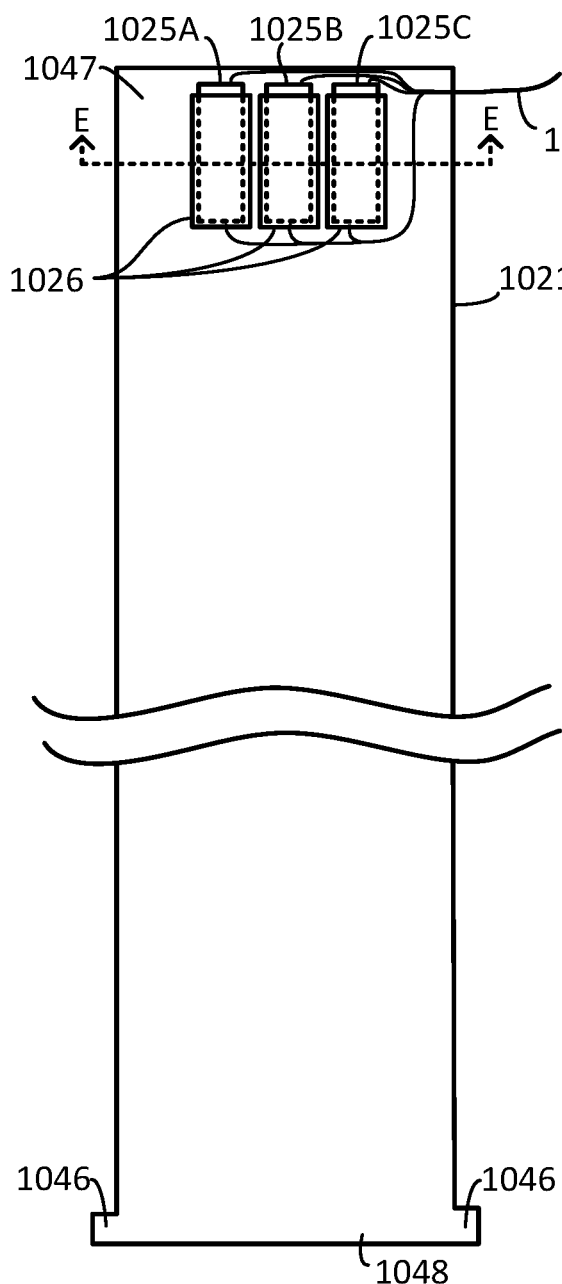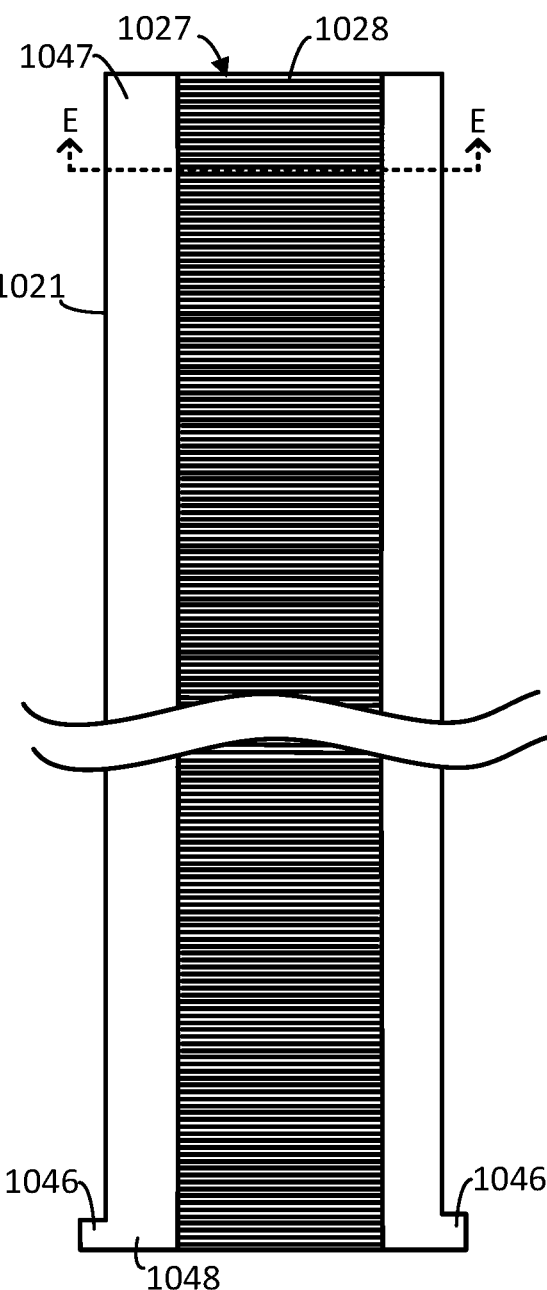
Fig. 13A
Fig. 13B
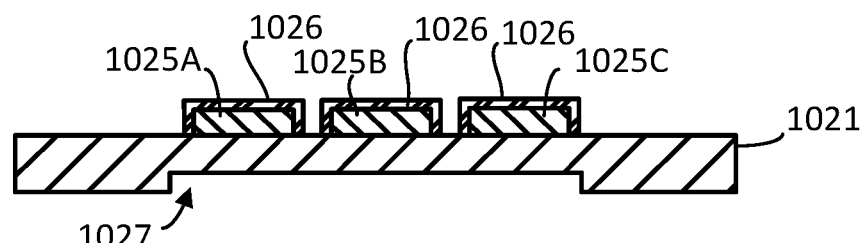
Fig. 13C

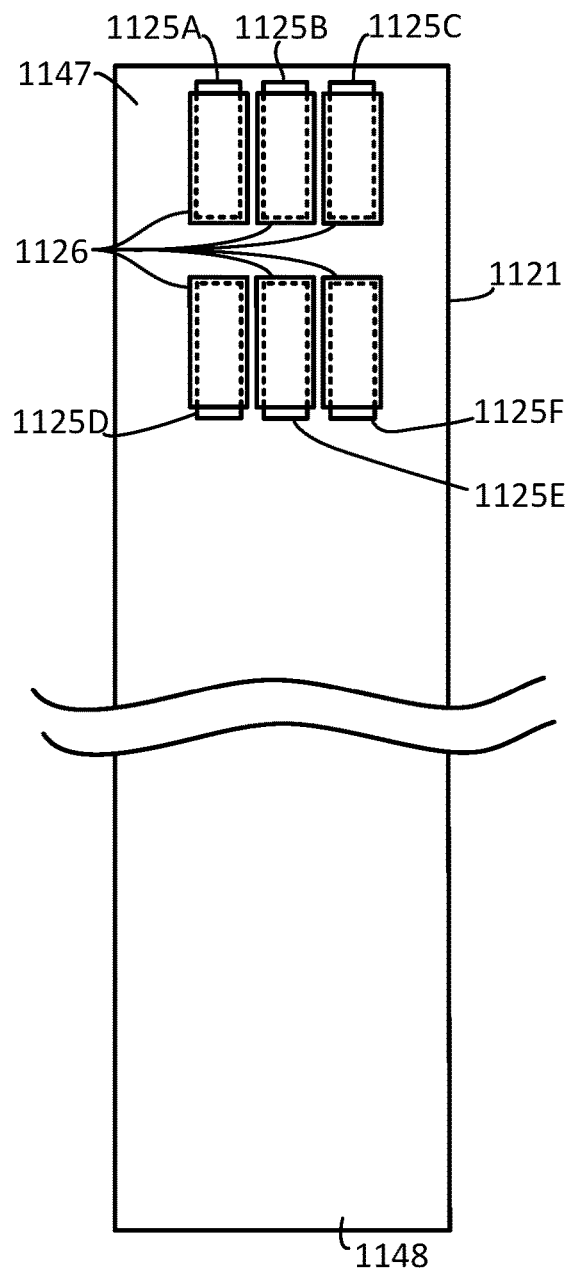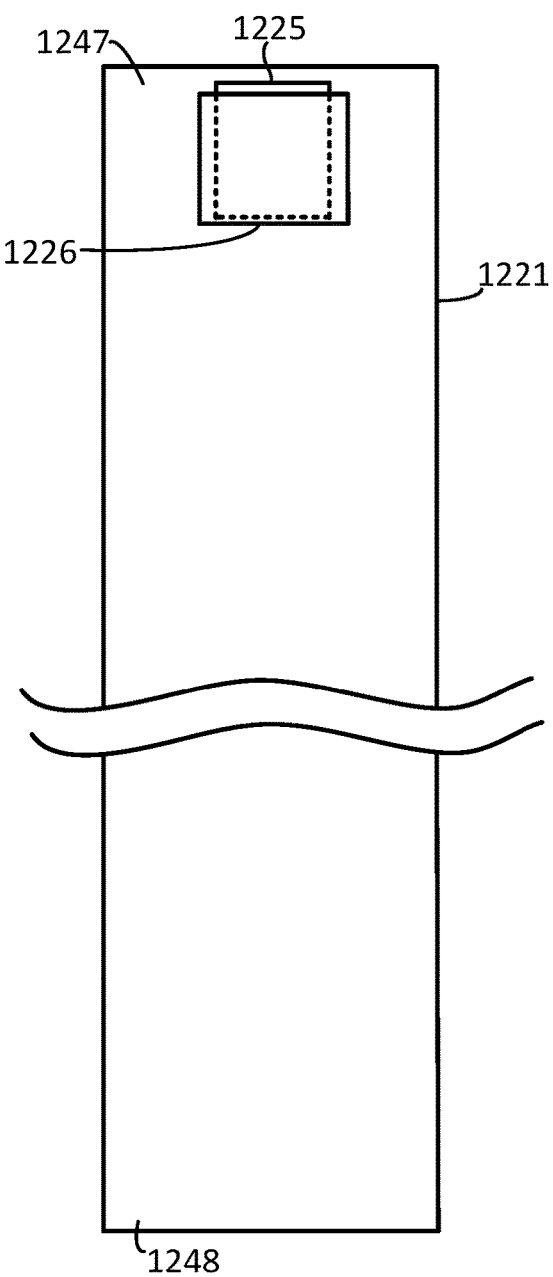
Fig. 14A
Fig. 14B

RADIAL EXPANSION AND CONTRACTION FEATURES OF MEDICAL DEVICES

CROSS-REFERENCE TO RELATED APPLICATION

This application claims the benefit of priority as a divisional application under 35 U.S.C. 121 of U.S. Non-Provisional application Ser. No. 15/159,801 filed on May 20, 2016, titled RADIAL EXPANSION AND CONTRACTION FEATURES OF MEDICAL DEVICES, which in turn claims the benefit of priority of U.S. provisional patent application No. 62/164,032, filed on May 20, 2015, titled RADIAL EXPANSION AND CONTRACTION FEATURES OF MEDICAL DEVICES, the disclosures of both of which are hereby incorporated by reference herein in their respective entireties.

FIELD OF THE INVENTION

This disclosure relates to medical devices, and more particularly to catheters and implantable devices which radially expand and contract to perform functions within the body.

BACKGROUND OF THE INVENTION

Medical devices can be inserted into patients percutaneously. Generally, medical devices have a low profile for minimally invasive introduction. However, such low profile design can inhibit the functionality of medical devices. For example, it may be advantageous for a catheter to assume a configuration having a profile larger than the needle, introducer, or guide catheter through which the medical device was introduced. Traditionally, such enlargement in profile has been accomplished by inflation of a balloon mounted on a catheter. However, use of balloons for expansion has limitations. Balloons have difficulty in creating fine or complex shapes. Balloons typically fully occlude passageways even if full occlusion is not wanted. Balloons lack precision in the degree of expansion. It can be difficult to develop sufficient hydraulic pressure through an inflation lumen being that the inflation lumens are narrow and long, two factors that contribute to pressure drop. Balloons are conventionally employed on catheters which extend ex vivo but are not typically used in fully implantable devices. Various embodiments of the present disclosure overcome these and/or other limitations of having expansion and/or contraction functionality that is not controlled by inflation of a balloon.

BRIEF SUMMARY OF THE INVENTION

Various embodiments concern radially expandable and/or contractable medical devices. The expansion and/or contraction may not be driven by a balloon, and may accordingly avoid some or all of the drawbacks of use a balloon for such a purpose.

In various embodiments, the expansion and/or contraction is driven by a radially adjustable structure. The diameter of the radially adjustable structure may be selectively increased and decreased. Multiple radially adjustable structures may be provided in a single medical device to allow for expansion and/or contraction at different locations. The medical devices may include catheters and/or implants.

The structure of the radially adjustable structure may be provided by a coiled strip. The strip may be, for example, a metal ribbon. The strip may be coiled so that the layers of the strip radially overlap each other, which can form the strip into a ring. Adjacent layers of the strip may be slid relative to one another to increase or decrease the diameter of the radially adjustable structure. The radially adjustable structure may be attached to a flexible catheter or implant in a manner such that the change in diameter of the radially adjustable structure forces or otherwise causes the diameter or other profile of the catheter or implant to also increase or decrease.

The change in diameter of the radially adjustable structure may be driven by one or more motors. The one or more motors may be mounted on the radially adjustable structure or may be located elsewhere on the medical device. The one or more motors may undergo expansion and contraction cycles to incrementally drive the radially adjustable structure through the change in diameter. For example, the reciprocation of the one or more motors may slide adjacent layers of the coiled strip relative to one another to increase or decrease the circumference of the ring formed by the coiled strip.

In the case of a coiled strip, the ring formed by the coiled strip may maintain a lumen during expansion and contraction. The ring may be located within the wall of a catheter or implant to allow the catheter or implant to also maintain a lumen during expansion and contraction. The lumen and/or exterior surface of the catheter or implant may increase or decrease in diameter along with the coiled strip.

Radial expansion may be the employed in a catheter to capture or otherwise remove an object from a body (e.g., by forming a funnel), implant a device, anchor the catheter, and/or therapeutically contact tissue (e.g., perform angioplasty or provide pressure input to a vessel and/or nerve), amongst other options. Radial expansion may be the employed in an implant to anchor the implant, restrict and/or open a vessel, anchor the implant, and/or therapeutically contact tissue (e.g., provide pressure input to a nerve), amongst other options. Radial contraction can similarly be used for various purposes.

In a first example, a medical device introducible into a patient, the medical device comprising: a flexible body having an outer diameter and an inner lumen, the inner lumen defining an inner diameter, the flexible body configured to undergo a movement cycle within the patient, the movement cycle comprising an expansion phase and a contraction phase, wherein one or both of the outer diameter and the inner diameter increases in the expansion phase, and wherein one or both of the outer diameter and the inner diameter decreases in the contraction phase; and one or more motors located within the flexible body, each motor configured to perform an actuation cycle in response to application of an electrical signal to the motor, wherein, for each iteration of the movement cycle of the flexible body within the patient, the one or more motors are configured to perform a plurality of the actuation cycles to drive the flexible body through either the expansion phase or the contraction phase.

In a second example, a medical device introducible into a patient, the medical device comprising an annular body, the annular body comprising a strip coiled to have overlapping layers, the annular body having a diameter, the annular body configured such that the overlapping layers of the strip slide relative to each other to increase the diameter of the annular body during an expansion phase and decrease the diameter of the annular body during a contraction phase. The diameter of the annular body may be an inner diameter of a lumen or an outer diameter of the annular body. One or more motors may drive either or both of the expansion phase and the contraction phase.

In a third example, a medical device comprising an body configured for in vivo introduction, a strip attached to the body and rolled into a ring such that layers of the strip radially overlap each other, and at least one motor. The at least one motor is actuatable by electrical energy and configured to, by said actuation, move the radially overlapping layers of the strip relative to one another and change a diameter of the ring.

In a fourth example, a medical device comprising a polymer body having a first diameter and configured for in vivo introduction, a strip attached to the polymer body, the strip rolled into a ring such that layers of the strip radially overlap each other. The ring has a second diameter. The strip is formed from a type of metal. The medical device further comprising at least one motor, the at least one motor attached to the strip and actuatable by electrical energy. The at least one motor is configured to change the second diameter of the ring by moving the radially overlapping layers of the strip relative to one another via actuation of the at least one motor. The ring is configured to one or both of expand in an expansion phase in which the ring applies force to the polymer body to cause the first diameter to increase and contract in a contraction phase in which the ring applies force to the polymer body to cause the first diameter to decrease. The at least one motor is configured to actuate to drive the ring through one or both of the expansion phase and the contraction phase to change the first and second diameters.

The scope of this disclosure is not limited to this summary. Further inventive aspects are presented in the drawings and elsewhere in this specification and in the claims.

BRIEF DESCRIPTION OF THE DRAWINGS

FIGS. 3A-B are perspective views of a catheter undergoing radial change.
FIGS. 3C-D are cross sectional views of the embodiment of FIGS. 3A-B, respectively.
FIGS. 7A and 7C are perspective views of an adjustable body radially changing.
FIGS. 7B and 7D are frontal views of the embodiments of FIGS. 7A, C, respectively.
FIGS. 9A-B, C are overhead and cross sectionals views, respectively, of a strip.

FIGS. 13A-C are overhead and cross sectional views, respectively, of a strip.
FIGS. 14A-B are overhead of views of strip configurations.

This disclosure makes use of examples to demonstrate various inventive aspects. The concepts presented in connection with a particular embodiment can be employed together with any other aspects presented in connection with the different embodiments. Thus, the presentation of the embodiments should be understood as demonstrating a number of open ended combinable options and not restricted embodiments. Changes can be made in form and detail to the various embodiments and features without departing from the spirit and scope of the invention.

DETAILED DESCRIPTION OF THE INVENTION

This disclosure generally relates to catheters and implantable devices that undergo movement cycles within a patient. The cycles can include expansion and contraction phases. During the expansion phase, catheters and implantable devices may expand to have a larger profile. During the contraction phase, the catheters and implantable devices may contract to have a smaller profile. The catheters and implantable devices may expand to have profiles larger or contract to have smaller profiles than when the catheters and implantable devices were first introduced into the body, previous to the expansion phase, and/or following the contraction phase. These and other aspects will be discussed and shown in connection with the following embodiments. It is noted that the embodiments are presented to demonstrate various inventive aspects. For the sake of clarity and practicality, all possible combinations of the various aspects are not presented herein as separate embodiments. Aspects of one embodiment can be combined and/or modified with those of a different embodiment. As such, the inventive scope of this disclosure is not limited to the particular embodiments disclosed.

Figure 1:
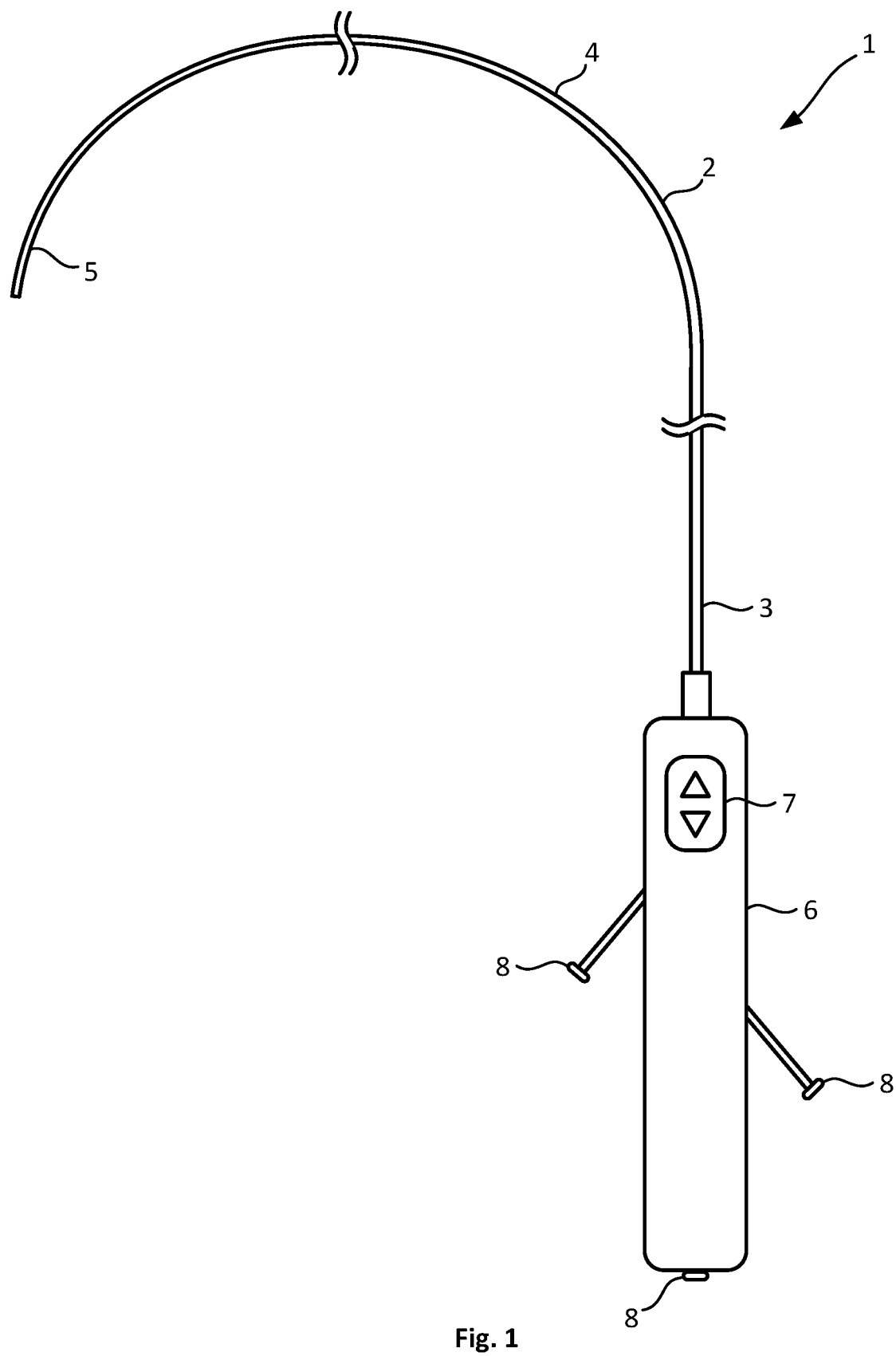
FIG. 1 is a schematic view of a catheter.

FIG. 1 shows a schematic view of a medical device 1. The medical device 1 includes a catheter 2 that is percutaneously insertable into a patient. For example, the catheter 2 can be inserted into a vessel or other pathway of the patient. Examples of pathways include the circulation system (e.g., veins, arteries, and/or heart, such as via the femoral artery), the respiratory system (nasal, trachea, larynx and bronchia, such as via the mouth), the digestive system (e.g., mouth, throat, esophagus, stomach, intestines, colon, anus, kidneys, bladder, urethra and various ducts, such as via the mouth, urethra, or anus), amongst others.

The catheter 2 includes a proximal section 3, a distal section 5, and an intermediate section 4 that is located between the proximal section 3 and the distal section 5. In various embodiments, the catheter 2 is a tube or other elongated flexible body that extends from the proximal section 3 to the distal section 5. At least in the form of a tube, the catheter 2 can be a round body. Round, as used herein, includes generally circular and elliptical profiles which need not be perfectly circular or elliptical. The tube or other elongated flexible body can be formed from polymer material, such as polyurethane, nylon, polyethylene terephthalate, polyether block amide, and/or silicone, amongst others. The catheter 2 may additionally or alternatively be formed from a metal such as, for example, a nickel-titanium alloy (i.e. Nitinol).

The medical device 1 is shown to include a handle 6. The proximal section 3 of the catheter 2 is connected to the handle 6. The handle 6 is sized to remain outside of the patient. The handle 6 includes a plurality of ports 8. The ports 8 can be in fluid communication with one or more lumens of the catheter 2. For example, the catheter 2 can include one or more internal lumens that extend the full length of the catheter 2 to connect with one or more of the ports 8, to allow passage of an elongated device (e.g., a guide wire) and/or fluids (drugs, contrast dye, etc.) through the catheter 2 and past its distal section 5.

The handle 6 includes a user input 7. User input 7 can include one or more buttons that are electrically connected to control circuitry (discussed later herein) housed within the handle 6 and/or connected to the handle 6. Such control circuitry can include a power source (e.g., a battery) and a circuit for generating one or more electrical signals based on user input (e.g., from the user input 7) to cause a portion of the catheter to expand and contract.

Figures 2A, 2B:
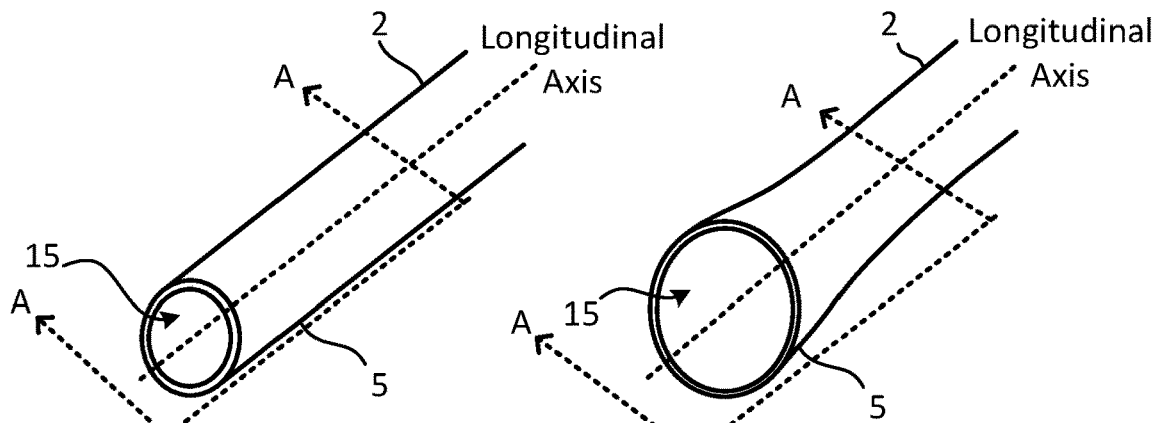
FIGS. 2A-B are perspective views of the catheter of FIG. 1 undergoing radial change.

FIG. 2A shows an enlarged schematic view of the distal section 5 of the catheter 2. As shown, at least part of the distal section 5 of the catheter 2 (and optionally the whole length of the catheter 2) includes a longitudinal axis. The longitudinal axis is orientated coaxial with the distal section 5 of the catheter 2. In other words, the longitudinal axis is orientated along at least part of the catheter 2 to extend through a radial center of the catheter 2. The distal section 5 includes a lumen 15, which as discussed previously can extend the full length of the catheter 2. The lumen 15 can be coaxial with the indicated longitudinal axis.

FIG. 2B shows the same view as FIG. 2A except that part of the distal section 5 has radially expanded relative to the state shown in FIG. 2A. Radial expansion, as used herein, refers to movement laterally outward from a radial center. The radial center may be at the longitudinal axis of the catheter or implantable device. Radial contraction, as used herein, refers to movement laterally inward toward the radial center. The lateral direction of expansion or contraction can be orthogonal to the longitudinal axis of the catheter or implantable device. While the order of FIGS. 2A-B and 2C-D show an expansion phase of a movement cycle, the same Figs. in the reverse order can represent a contraction phase of the movement cycle.

As shown in FIG. 2B, a funnel has been formed from the radial expansion of the distal section 5, the funnel defined by a transition in the inner diameter of the lumen 15 along the longitudinal axis of the distal section 5. It is noted that this radial expansion is orthogonal to the longitudinal axis of the catheter 2. While in FIG. 2A, the lumen 15 has a consistent inner diameter along the full length of the catheter 2 (or at least along the distal section 5), the lumen 15 is larger distally and narrows proximally along the distal section 5 in the state shown in FIG. 2B. In this way, a circumferential inner surface of the catheter 2 that defines the inner lumen 15 is sloped inwardly in the proximal direction to form an inner funnel.

Figure 2C:
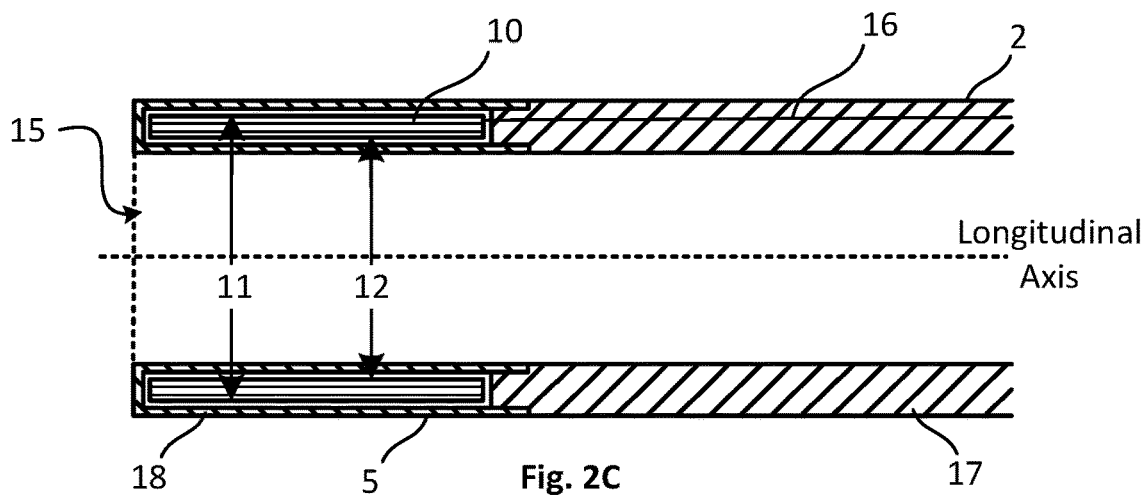
FIGS. 2C-D are cross sectional views of the embodiment of FIGS. 2A-B, respectively.
Figure 2D:
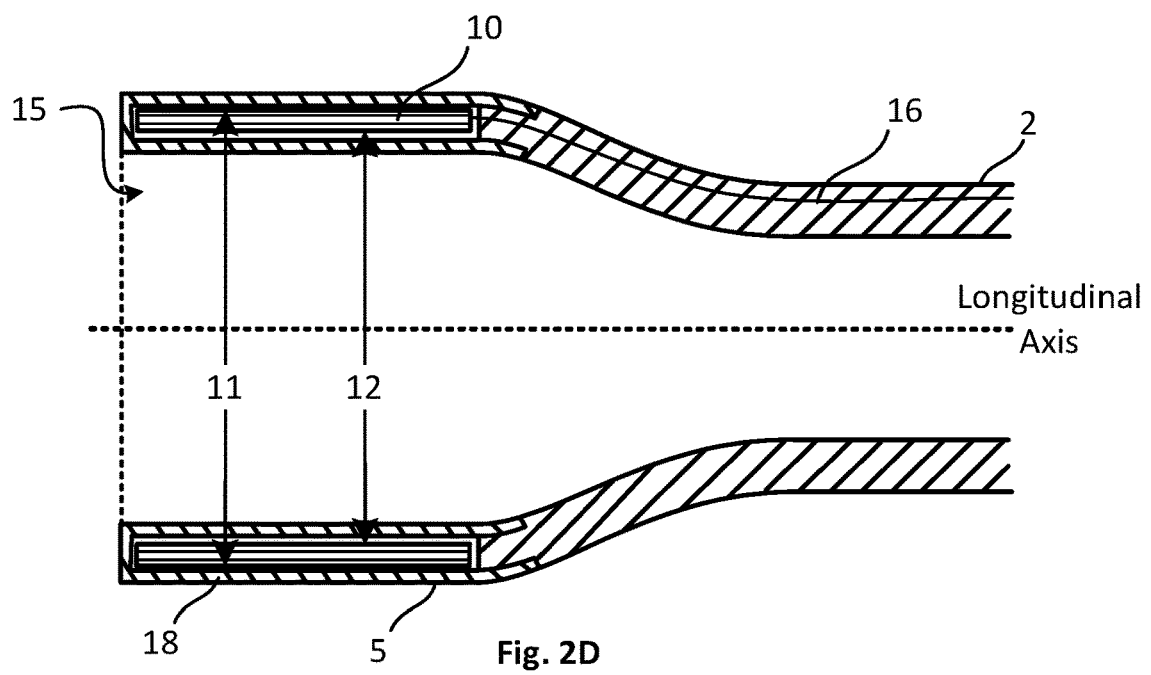

FIG. 2C is a cross sectional view taken along plane AA of FIG. 2A while FIG. 2D is a cross sectional view taken along the same plane AA of FIG. 2B. FIGS. 2C-D show one option for how radial expansion and/or contraction can be carried out. As shown in FIGS. 2C and 2D, the catheter 2 is formed from catheter body material 17. The catheter body material 17 can be a polymeric material (e.g., any material referenced herein) formed into the tube shape shown in FIGS. 2A-D. The catheter 202 can be a round body. The distal section 5 includes compliant material 18. Compliant material 18 can be a polymeric material (e.g., any material referenced herein), and in some embodiments is a different type of polymeric material as the catheter body material 17. In some other embodiments, the compliant material 18 can be the same type of material as the catheter body material 17. In some embodiments, the compliant material 18 is more flexible (e.g., has a lower durometer and/or lower elastic modulus) than the catheter body material 17. In some embodiments, the compliant material 18 can be silicone while the catheter body material 17 can be a stiffer polymer such as polyurethane, nylon, or PEBAX. The compliant material 18 can be heat bonded, sonically welded, or adhered (e.g., with epoxy) to the catheter body material 17. Each of the catheter body material 17 and the compliant material 18 form a body.

The radial expansion of the catheter 2 is caused by expansion of the radially adjustable structure 10. The radially adjustable structure 10 is in the shape of a ring in the embodiment shown. As further discussed herein, the radially adjustable structure 10 increases in diameter between the states of FIGS. 2C-D to force the body of the catheter 2 along the distal section 5 to expand in inner diameter, outer diameter, and circumference.

The radially adjustable structure 10 is in the shape of an annular body which, as referenced herein, can have a circular or ovular profile while not necessarily being perfectly circular, ovular, or otherwise uniform in circumferential profile. As shown, the radially adjustable structure 10 is located at the distal section 5 of the catheter 2. The radially adjustable structure 10 is distal and remote from the proximal section 3 as well as the intermediate section 4 of the catheter 2. During assembly, the compliant material 18 can be placed around the radially adjustable structure 10 and then the compliant material 18 can be attached to the catheter body material 17. The radially adjustable structure 10 is mounted on the distal section 5 of the catheter 2. The radially adjustable structure 10 is embedded within the distal section 5 of the catheter 2 in the illustrated embodiment. More specifically, the radially adjustable structure 10 is contained within the material of the catheter 2 (e.g., the compliant material 18 and/or the catheter body material 17) such that the expansion contraction element 10 does not have a surface that is exposed (e.g., exposed to body tissue) outside of the catheter 2. In some embodiments, the radially adjustable structure 10 may be neither exposed on an outer surface that defines an outer circumference of the catheter 2 nor on an inner surface that defines the inner lumen 15. However, in various other embodiments, the radially adjustable structure 10 can be exposed, such as one or both of on the outer surface that defines the outer circumference of the catheter 2 and the inner surface that defines the inner lumen 15. For example, the radially adjustable structure 10 can be located around the exterior of the catheter body material 17 or entirely inside the lumen 15. As shown in FIGS. 2C-D, the radially adjustable structure 10 is coaxial with the catheter 2, particularly with respect to the longitudinal axis.

The radially adjustable structure 10 is electrically connected to control circuitry (e.g., located in the handle 6) by conductor 16. The conductor 16 can extend from the radially adjustable structure 10 to the handle 6 to electrically connect with circuitry so as to conduct electrical signals between the circuitry and the radially adjustable structure 10. The conductor 16 can represent a single conductor or multiple conductors supporting different electrical channels, for example. The conductor 16 can be formed from conductive metal (e.g., copper, MP35N, silver, and/or gold) that is stranded, braided, or coiled or taking other conductor forms. Conductors 16, as well as any conductor element referenced herein, can be electrically insulated by a thin polymer coating, such as polyurethane. The conductor 16 can extend within a lumen defined in the catheter body material 17.

FIGS. 2A-5D show various ways in which radially adjustable structures can be incorporated into catheters and implantable medical devices. The radially adjustable structure 10, as well as the medical device 1, can be configured in various ways to carry out radial expansion and/or contraction. For example, the radially adjustable structure 10 can be configured in any way referenced herein, such in the manners shown and described in connection with FIGS. 6A-17C. FIGS. 18A-24 show various applications for catheters and implantable medical devices having expansion and/or contraction capabilities.

FIG. 3A-B shows a perspective view of a distal section 105 of the catheter 102 at different states of a movement cycle. FIGS. 3C-D show cross sectional views along plane BB of FIGS. 3A-B, respectively. For this disclosure, components sharing the first two digits of their reference numbers (e.g., 2, 102, 202, 302, etc. or 10, 110, 210, 310, etc.) can have similar configurations or may even be the same embodiment amongst the various illustrated and described embodiments. For example, catheter 102 can be identical to catheter 2 except for those aspects shown or described to be different. For the sake of brevity, common aspects (e.g., materials, features, functions, properties, options, alternatives, etc.) are not repeated for different views and embodiments but can be realized in all other embodiments. In view of this disclosure being a series of examples demonstrating various interchangeable aspects and features, for all referenced embodiments, an aspect described or shown for one embodiment can be implemented in another referenced embodiment or as an alternative embodiment incorporating disparate aspects.

Returning to the embodiment of FIGS. 3A-D, a radially adjustable structure 110 is shown embedded within the wall of the distal section 105 of the catheter 102. In FIG. 3C, the radially adjustable structure 110, which can take the form of a ring, sits within a trench formed by the catheter body material 117 and which that extends entirely around the circumference of the catheter body material 117. Encircling this trench and the radially adjustable structure 110 is a layer of compliant material 118. The radially adjustable structure 110 is electrically connected to a conductor 116. The compliant material 118 may be attached to the catheter body material 117 at the distal and proximal ends of the compliant material 118 but not directly attach to the catheter body material 117 in the middle portion of the compliant material 118 that is directly over the radially adjustable structure 110.

The radially adjustable structure 110 increases in diameter between the states of FIGS. 3C-D to force the body of the catheter 102 along the distal section 105 to expand in outer diameter and circumference. The distal section 105 is shown to expand at an expansion/contraction portion of the catheter 102 in FIGS. 3B and 3D. As compared to the embodiment of FIGS. 2A-D, a funnel is not formed by the expansion at the distal opening of the catheter 102 and the outer diameter of the catheter 102 that is distal to the expansion/contraction portion (e.g., to the distal tip of the catheter 102) is consistent and does not change due to the expansion. Rather, a bulb is formed along an intermediary portion of the distal section 105 of the catheter 102. Additionally or alternatively, a bulb could be formed along an intermediate section (e.g., corresponding to intermediate section 4 of the embodiment of FIG. 1) of the catheter 102 depending on the location of the radially adjustable structure 110. The radial expansion increases the outer diameter and circumference of the catheter 102. As shown in FIG. 3D, the inner diameter of the inner lumen 115 is not increased by the expansion of the radially adjustable structure 110. However in some other embodiments, the inner diameter of the inner lumen 115 along this expansion/contraction portion is increased by the expansion of the radially adjustable structure 110 in similar manner to the increase in the inner diameter of the lumen 15 as shown in FIGS. 2C-D. The increase in outer diameter without an increase in the inner diameter of the catheter 102, as shown in FIG. 3D, can be due to the use of a more flexible material for the compliant material 118 than the catheter body material 117 and/or by not anchoring the radially adjustable structure 110 to the catheter body material 117 so that the radially adjustable structure 110 can expand independently of the catheter body material 117. While the order of FIGS. 3A-B and 3D-C shows an expansion phase of a movement cycle, it will be understood that the same Figs. in the reverse order can represent a contraction phase of the movement cycle.

Figure 4A:
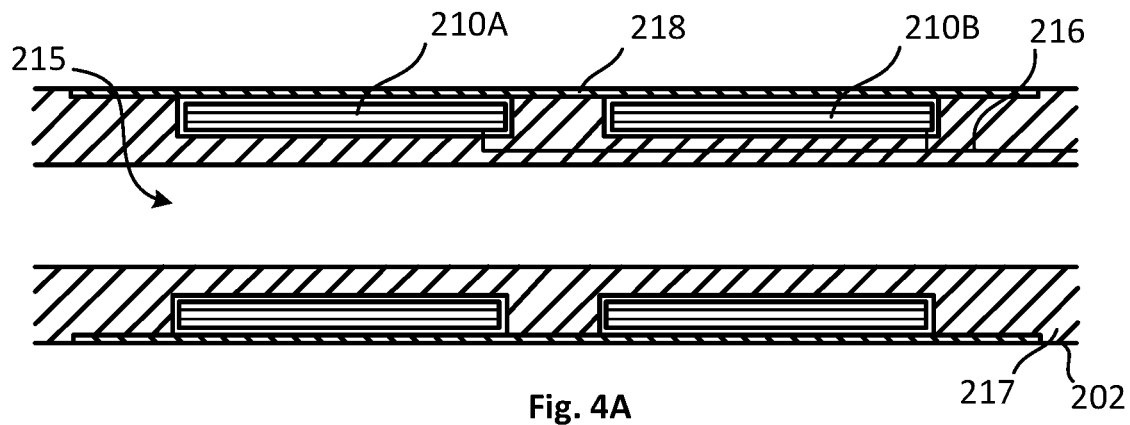
FIGS. 4A-C are cross sectional views of a medical device undergoing radial change.
Figure 4B:
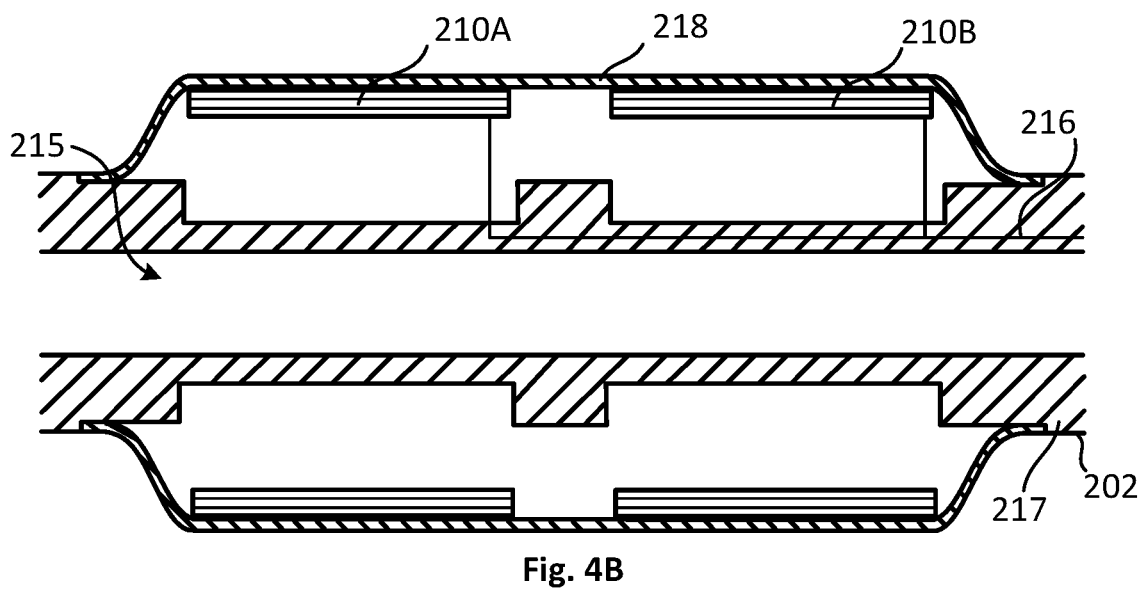
Figure 4C:
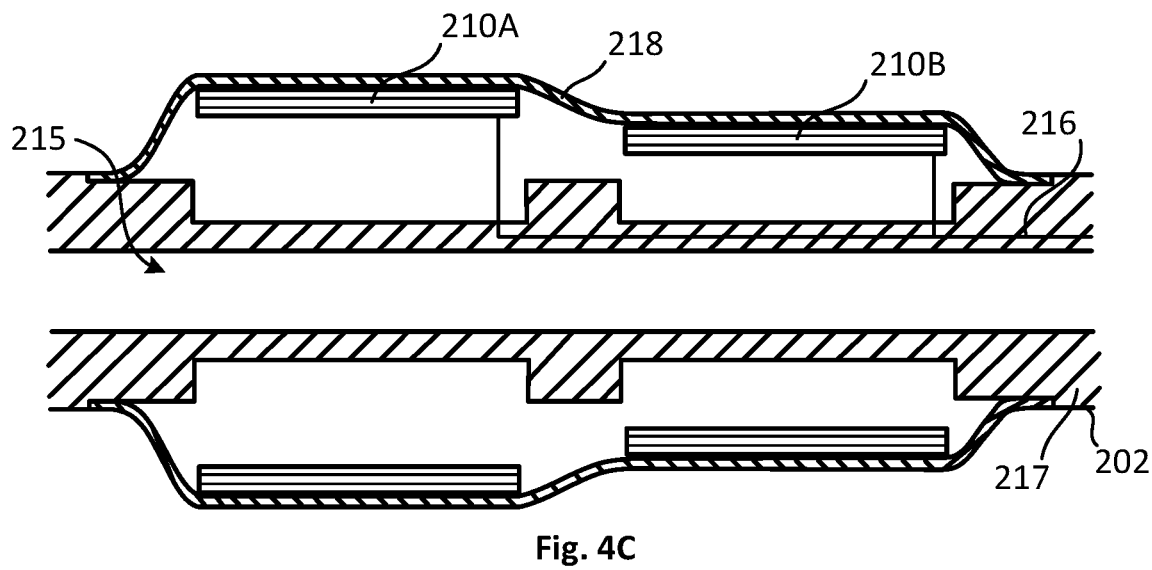

The embodiment of FIG. 4A-C shows multiple radially adjustable structures 210A-B. FIGS. 4A-C show catheter body material 217 including multiple trenches in which a first radially adjustable structure 210A and a second radially adjustable structure 210B can be seated. The first radially adjustable structure 210A is located wholly distally with respect to the second radially adjustable structure 210B while the second radially adjustable structure 210B is located wholly proximally with respect to the first radially adjustable structure 210A. Both of the first and second radially adjustable structures 210A-B are covered by a layer of compliant material 218. Both of the first and second radially adjustable structures 210A-B may alternatively be covered by a layer of the catheter body material 217 instead of the layer of compliant material 218. As shown in FIGS. 4B-C, both of the first and second radially adjustable structures 210A-B can expand at the same time to increase the outer diameter of the catheter 202.

Both of the radially adjustable structures 210A-B can be independently controllable with respect to each other, such that each can be expanded or contracted from the same first diameter (or different initial diameters) to different secondary sizes at the same time. As shown in FIG. 4C, the first and second radially adjustable structures 210A-B are expand to different diameters such that the first radially adjustable structure 210A is expanded to have a larger outer diameter than the second radially adjustable structure 210B. This forces the body of the catheter 202 to have different outer diameters along different longitudinal sections of the catheter 202 at which the radially adjustable structures 210A-B are respectively located. While the order of FIGS. 4A-B shows an expansion phase of a movement cycle, it will be understood that the same Figs. in the reverse order can represent a contraction phase of the movement cycle.

Figures 5A, 5B, 5C:
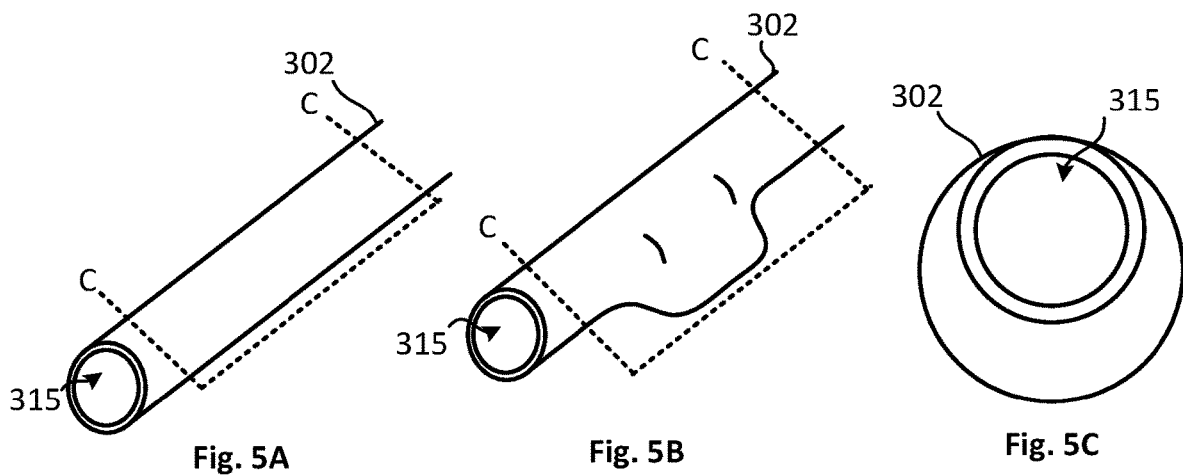
FIGS. 5A-B are perspective views of a medical device undergoing radial change.
FIG. 5C is a frontal view of the medical device of FIG. 5B.
Figure 5D:
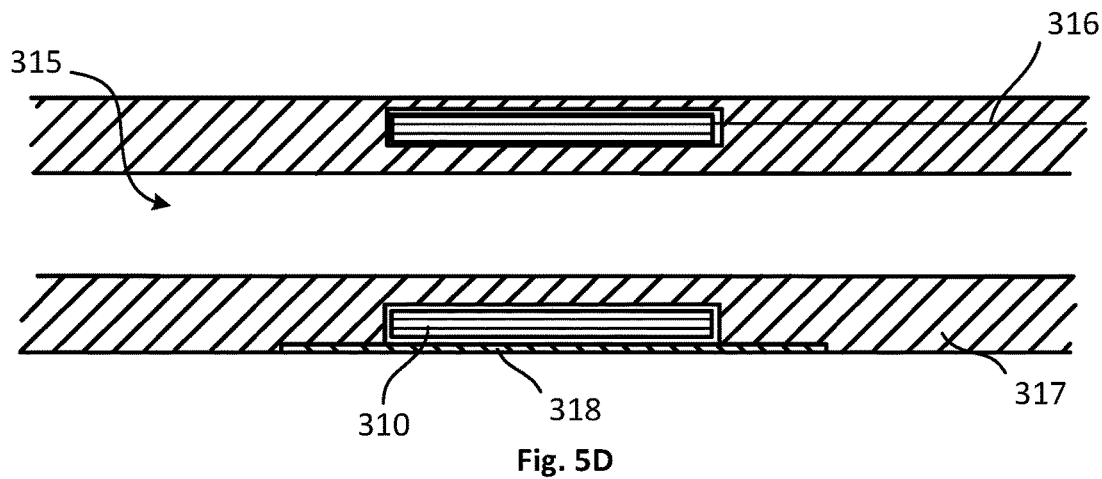
FIGS. 5D-E are cross sectional views of the device of FIGS. 5A-B, respectively.
Figure 5E:
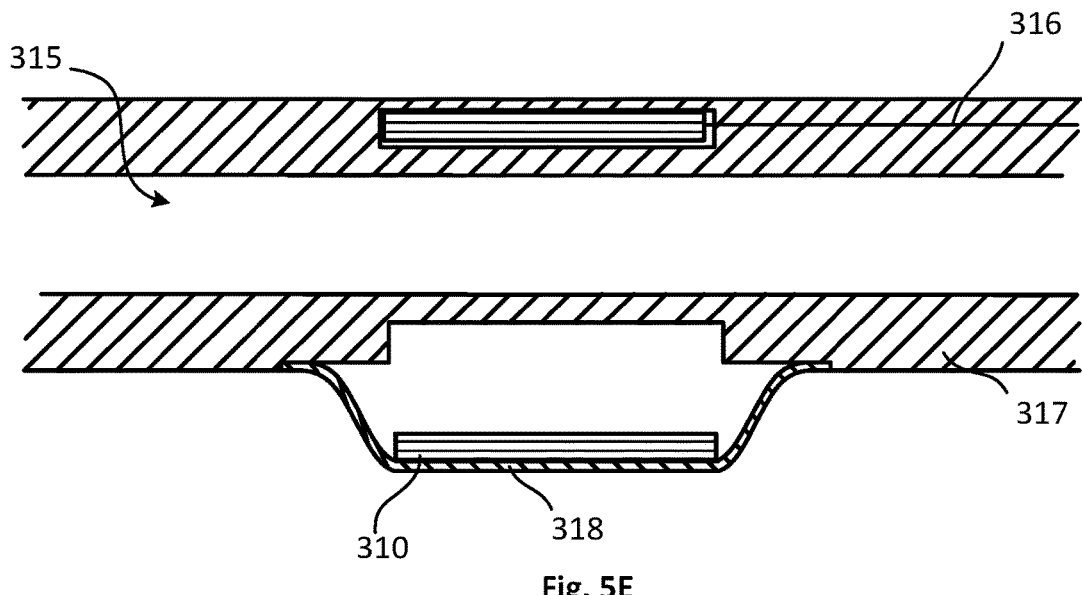

FIGS. 5A-B show a perspective view of a distal section 305 of the catheter 302. FIG. 5C shows a front end view of a distal section 305 of the catheter 302 as expanded. FIGS. 5D-E show cross sectional views along plane CC of FIGS. 3A-B, respectively. While the order of FIGS. 5A-B and 5D-E show an expansion phase of a movement cycle, it will be understood that the same Figs. in the reverse order can represent a contraction phase of the movement cycle.

A radially adjustable structure 310 is embedded within the distal section 305 of the catheter 302. The radially adjustable structure 310 can be similar to any of that disclosed herein, but the radial expansion profile is different from the previous embodiments. The previous embodiments generally expand evenly around the longitudinal axis of the catheter. In FIGS. 5A-E, the expansion is greater on one lateral side of the catheter 302 than another side. This asymmetry of expansion is achieved by providing stiffer catheter body material 317 around a portion of the radially adjustable structure (e.g., the top side as shown in FIG. 5D) while a more compliant material 318 is provided along one or more other sides (e.g., the bottom side as shown in FIG. 5D). In expanding, the radially adjustable structure 310 may tend to radially expand in the direction of least resistance, which is towards the lower modulus compliant material 318 instead of the stiffer catheter body material 317. While different types of materials are used in this embodiment to control the direction of radial expansion, in other embodiments, the same material can be used entirely around an expansion/contraction structure but the walls of the material can be thinner along a first circumferential section (fostering greater radial expansion and/or contraction there-along) and thicker in a second circumferential section (fostering lesser radial expansion and/or contraction there-along).

Figure 6A:
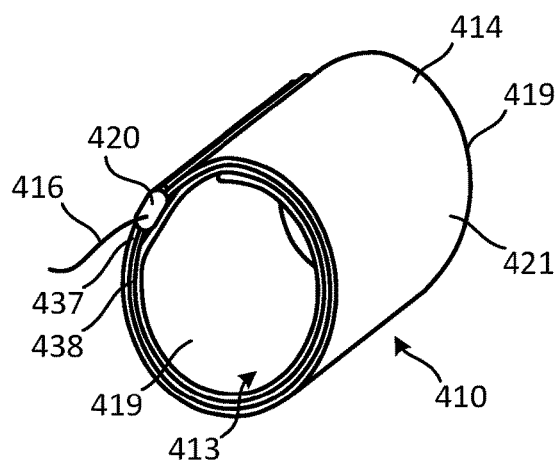
FIGS. 6A, C are perspective views of an adjustable body radially changing.
Figure 6B:
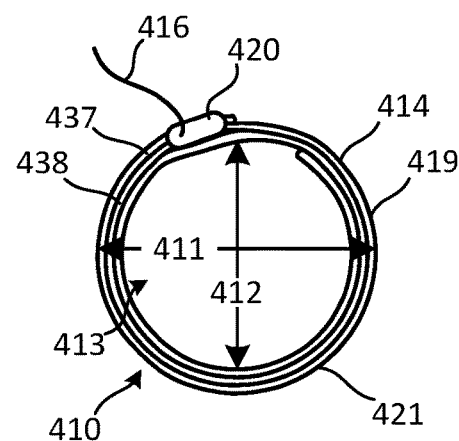
FIGS. 6B, D are frontal views of the embodiments of FIGS. 6A, C, respectively.
Figure 6C:
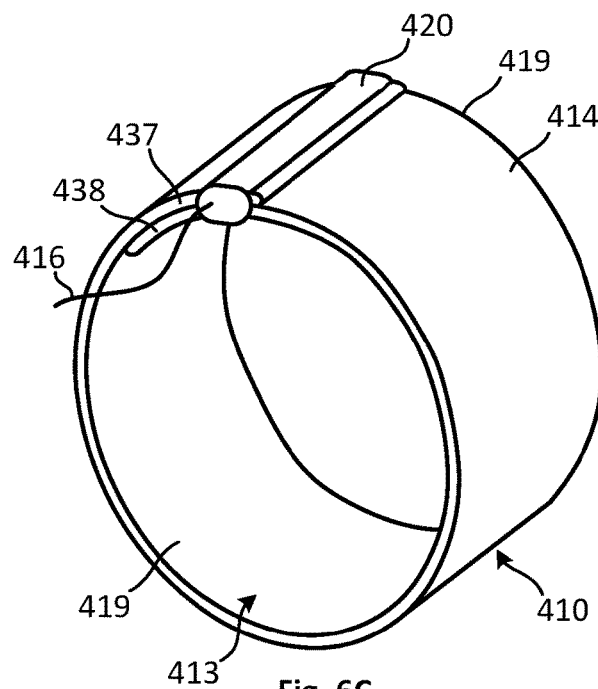
Figure 6D:
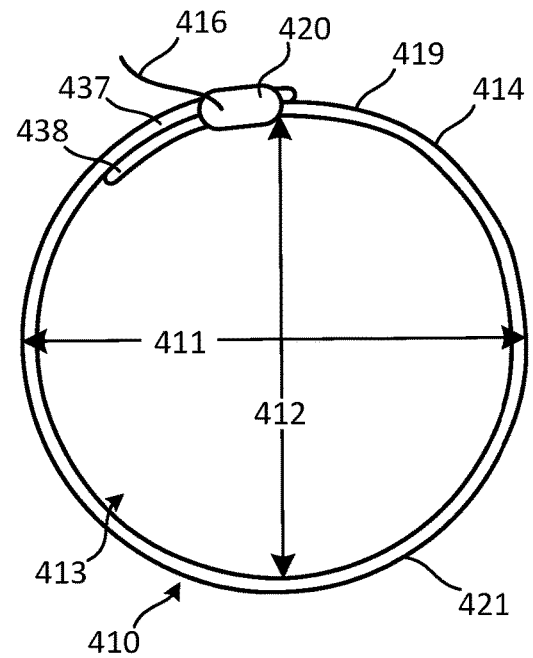

FIGS. 6A-D show a radially adjustable structure 410. The radially adjustable structure 410 can correspond with any radially adjustable structure referenced herein, such as for use in the embodiments of FIGS. 2A-5E and 18A-24. FIG. 6A shows a perspective view of a radially adjustable structure 410. FIG. 6B shows a front view of the radially adjustable structure 410 in the same state as in FIG. 6A. The radially adjustable structure 410 is in a relatively small or contracted state in FIG. 6A-B. FIGS. 6C-D shows the same views as in FIGS. 6A-B, respectively, of the radially adjustable structure 410 except that the radially adjustable structure 410 is in a relatively larger or expanded state in FIGS. 6C-D. While the order of FIGS. 6A-B and 6C-D show an expansion phase of a movement cycle, it will be understood that the same Figs. in the reverse order can represent a contraction phase of the movement cycle.

The radially adjustable structure 410 comprises a strip 421 rolled into a ring. The ring is round. The strip 421 is coiled upon itself to form multiple layers. At least some of the layers radially overlap each other. For example, in the smaller state of FIGS. 4A-B, all layers radially overlap each other while in the larger state of FIGS. 4C-D, there is a single layer about a circumferential portion of the radially adjustable structure 410. The change in the number of layers corresponds to the change in diameter of the radially adjustable structure 410 as during the movement cycle the layers are caused to slide relative to each other (e.g., a layer can slide clockwise or counter clockwise relative to an adjacent layer) to increase or decrease the circumference of the radially adjustable structure 410 which changes the diameter.

The strip 421 has two opposite ends of its long axis (shown in FIGS. 9A-C). When rolled into the radially adjustable structure 410, the two ends are free with respect to each other such that the ends of the strip 421 can move (e.g., slide) relative to one another. The strip 421 is resistant to collapsing due to being coiled into a tubular shape. The coiling of a strip 421 has the added benefit that the strip 421 can be expanded and contracted while maintaining a lumen 413.

The strip 421 can be ribbon. The strip 421 can be formed from metal, such as stainless steel, aluminum, and/or Nitinol (i.e. a nickel titanium alloy), or other metal element or alloy. In some embodiments the strip 421 can be formed from a polymeric material, preferably stiff, such as high density polyethylene and polyamide, amongst other options. The strip 421 can include a first surface 414. The first surface 414 can define an outer surface, outer circumference, and outer diameter 411 of the radially adjustable structure 410 as shown in FIGS. 6B and 6D. The strip 421 includes a lumen 413 having an inner diameter 412. The strip 421 can include a second surface 419. The second surface 419 can define an inner surface, lumen 413, inner circumference, and inner diameter 412 of the radially adjustable structure 410.

The strip 421 is wrapped around itself in multiple layers including a first layer 437 and a second layer 438. The first layer 437 is radially outward from, but in contact with, the second layer 438. As shown by comparing FIGS. 6A-B to FIGS. 6C-D, respectively, the layers of the strip 421 can slide relative to each other (e.g., in clockwise and counter clockwise orientations about a radial center) to expand (going from FIGS. 6A-B to FIGS. 6C-D) and contract (going from FIGS. 6C-D to FIGS. 6A-B) the radially adjustable structure 410. For example, FIGS. 6A-B show three overlapping layers along a portion of the radially adjustable structure 410 and two overlapping layers elsewhere. In FIGS. 6C-D, the radially adjustable structure 410 is expanded to include only a single layer of the strip 421 around much of the circumference of the radially adjustable structure 410 yet the first layer 437 of the strip 421 still overlaps with the second layer 438 of the strip 421 over a portion about the circumference of the radially adjustable structure 410. In some embodiments, the radially adjustable structure 410 may always have multiple overlapping layers of the strip 421 about the entire circumference of the radially adjustable structure 410 in both expanded and contracted states such that there is no circumferential portion along which the radially adjustable structure 410 is formed by only a single layer of the strip 421.

The radially adjustable structure 410 can be part of a catheter, implantable device, or other device, such as any device referenced herein. Therein, the radially adjustable structure 410 can have a proximal terminus and a distal terminus and a length therebetween. The length of the radially adjustable structure 410 can be orientated along the longitudinal axis of the catheter, implantable device, or other device. In some embodiments, the length of the radially adjustable structure 410 is in the range of 0.5 centimeters to 3 centimeters, or in the range of 2 millimeters to 20 millimeters, although smaller and larger lengths may be utilized depending on the application.

In coiling the strip 421 into the radially adjustable structure 410 shown, the strip 421 can be strained in the manner of a spring, such that the strip 421 is mechanically biased to expand and uncoil (and in some cases, biased to lay flat as shown in FIGS. 9A-C). As such, the transition from the smaller outer diameter 411 and inner diameter 412 in FIGS. 6A-B to the larger outer diameter 411 and inner diameter 412 in FIGS. 6C-D can represent a lessening degree of strain in the spring (e.g., relaxation with less stored energy). A transition from the larger outer diameter 411 and inner diameter 412 in FIGS. 6C-D to the smaller outer diameter 411 and inner diameter 412 in FIGS. 6A-B can represent a straining of the spring and an increase in potential energy built up in the radially adjustable structure 410. As discussed further herein, a motor can drive the radially adjustable structure 410 from this larger state in FIGS. 6C-D down to the smaller state in FIGS. 6A-B, whereas merely releasing one or more mechanical restraints on the rolled strip 421 allows the radially adjustable structure 410 to release stress in transitioning from the smaller state in FIG. 7A-b to the larger state in FIG. 7C-D. In some embodiments the strip 421 is coiled and set so that it is more relaxed in a smaller state and is strained when expanded to have a larger state.

A bracket 420 (further shown in FIGS. 8A-B) accepts two layers of the coiled strip 421 within itself. Specifically, the bracket 420 accepts the first layer 437 and the second layer 438 within a space defined within the bracket 420. The bracket 420 can be rigidly attached to the first layer 437 formed by one end of the strip 421, such as by welding or riveting. In various embodiments, the bracket 420 is rigidly attached to the outer most layer of the strip 421 as coiled, which in the embodiment of FIGS. 6A-D is the first layer 437, and may be attached at or near the end of the strip 421. The bracket 420 serves to press the first and second layers 437, 438 (or other layers) close to or against one another to maintain the proximity of adjacent layers which helps facilitate forcing the layers to slide relative to one another. Conductor 416 can be supported by the bracket 420 and electrically connects control circuitry to one or more motors that act upon the coiled strip 421 to move the layers relative to one another and drive the expansion and contraction shown in FIGS. 6A-D, as further discussed herein. The bracket 420 being attached to the outermost layer of the coiled strip 421, and the second outermost layer of the strip 421 being threaded through the space in the bracket 420, prevents the outermost layer from peeling off and away from the rest of the layers. The innermost layer may not need to be secured because it is biased outwardly and thus may tend to stay close to the second inner most layer of the strip 421. The bracket 420 may function as a buckle through which the strip 421 is threaded and which holds the layers and/or ends of the strip 421 together.

As shown, the bracket 420 is positioned against or along the outer first surface 414 but is not against or along the inner second surface 419 in FIGS. 4A-D. As shown, the bracket 420 is wrapped around two adjacent layers of the strip 421 such that the bracket 420 is positioned against at least one of the inner circumference and the outer circumference of the ring (just the outer circumference in FIGS. 4A-B but both of the inner and outer circumferences in FIGS. 4C-D). As shown, the bracket 421 is located on a first section of the outer circumference of the coiled strip 421 but is not located on a second section of the outer circumference of the coiled strip 421, and the second section is longer than the first section.

It is noted that the illustrated strip 421 embodiment is coiled such that each outer layer aligns proximally and distally with the layer beneath it and does not extend proximally or distally of the layers beneath or above it. As such, the innermost layer extends distally and proximally to the same extent as the outermost layer, and vice versa, and this holds true for each successive layer. For at least this reason, the strip 421 does not take the shape of a helix. It is noted that despite radial expansion and contraction, the length of the strip 421 along the longitudinal axis did not change. Whether in an expanded or contracted state, the radially adjustable structure 410 does not extend any more distally or proximally as compared to any other expanded or contracted state. Thus, when placed in a catheter body, implantable device, or other medical device, the radially adjustable structure 410 can radially expand and contract without expanding and contracting along the longitudinal axis of the catheter. However, not all embodiments are so limited as to not expand longitudinally.

FIG. 7A-D illustrates an alternative configuration for a strip 521 coiled into a ring having a dynamic diameter. Specifically, while the bracket 420 in the configuration of FIGS. 6A-D is attached to the outermost layer of the coiled strip 421 and is located along the first surface 414 (as least in the smaller state of FIGS. 6A-B), the bracket 520 in the configuration of FIGS. 7A-D is instead attached to the innermost layer 539 and end of the coiled strip 521. In this configuration, the strip 521 is mechanically biased to coil up in a small ring. The lowest potential energy state of the coiled strip 521 is when the outer diameter 511 and the inner diameter 512 are relatively small and there is greater potential energy wound into the spring when the strip 521 is caused to expand to have a greater outer diameter 511 and inner diameter 512. The bracket 520, being attached (e.g., by welding or riveting) to the innermost layer 539 and end of the coiled strip 521, and the second most inner layer 545 being threaded through a space within the bracket 520, maintains the patency of the lumen 513 by the end of the inner most layer 539 of the strip 521 not peeling away into the center of the lumen 513. The end of the outermost layer of the strip 521 may not need to be secured because it is biased inward and therefore not inclined to separate from the other layers. A conductor 516 can extend through the bracket 520 or otherwise connect with electrical components on the strip 521. The strip 521 can include a first surface 514 that defines an outer surface and outer diameter 511 of the annular body 510. The strip 521 can include a second surface 519 that defines an inner surface, lumen 513, and inner diameter 512 of the annular body 510. As shown, the bracket 520 is positioned against or along the second surface 519 but is not against or along the first surface 514.

It is noted that while a single bracket is shown on the coiled strip in the embodiments of FIGS. 6-7, two or more brackets can be provided on a coiled strip. For example, two brackets can be attached to the opposite ends of the strip, respectively. The two brackets can be attached to the inner most and outer most layers of the strip to be on the inner and outer surfaces of the ring as shown (separately) in FIGS. 6A-7D. Additionally or alternatively, multiple brackets (e.g., two, three, four, etc.) can be attached to the same layer (e.g., innermost or outermost) to lengthen the distance along the strip along which the layers are forced against one another.

Figure 8A:
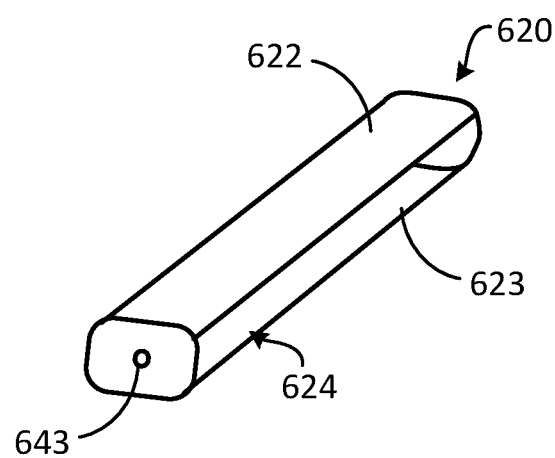
FIGS. 8A-B are perspective and frontal views of a bracket, respectively.

FIG. 8A shows a perspective view of a bracket 620. The bracket 620 can correspond to any bracket referenced herein, such as bracket 420 or 520. The bracket includes a top portion 622 and a bottom portion 623 and a space 624 defined between the top portion 622 and the bottom portion 623. Side portions at opposite ends connect the top portion 622 to the bottom portion 623. An aperture 643 through a side portion allows one or more conductors to be routed from outside the bracket 620 to inside the bracket 620 to connect with any electrical elements on the strip or within the space 624, such as a motor. It is within the space 624, and between the top portion 622 and the bottom portion 623, that the two (or other number) of adjacent layers of the strip (any strip referenced herein, such as strips 421, 521) are located to help the strip maintain the annular shape (e.g., as in FIGS. 6A-7D). These two layers can be the two outer most layers or the two inner most layers of the annular body, depending on the bias of the strip (e.g., biased to flatten or curl). Moreover, one or more motors can be located between the top portion 622 and the bottom portion 623 to drive the movement cycles.

Either of the top portion 622 or the bottom portion 623 of the bracket 620, depending on which is outermost or innermost and the bias of the strip 621, can be attached (e.g., welded, riveted, or glued with epoxy) to the strip. For example, if the bracket 620 accepts the two outermost layers of the strip (e.g., in FIGS. 6A-D), then the top portion 622 can be orientated radially outward from the strip (and the bottom portion 623), and the top portion 622 can be attached to an exterior surface (e.g., the first surface 414 of FIGS. 6A-D) of the outermost layer of the strip. If the bracket 620 accepts the two innermost layers of the strip (e.g., in FIGS. 7A-D), then the bottom portion 623 can be orientated radially inward from the strip (and the top portion 622) and the bottom portion 623 can be attached to the radial center-facing surface (e.g., the second surface 519 of FIGS. 7A-D) of the innermost layer of the strip.

Figure 8B:
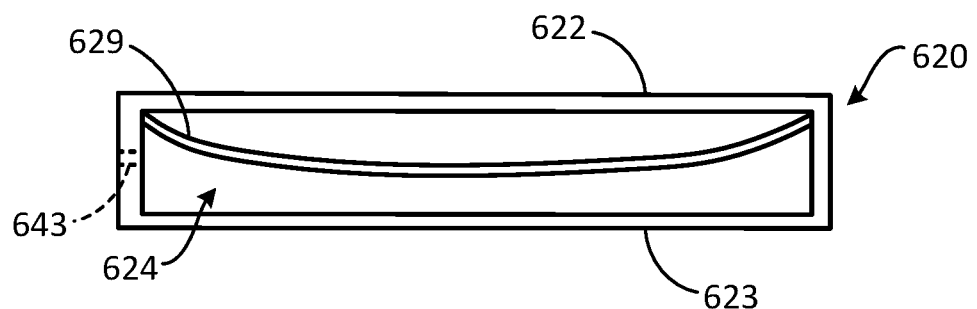

The bracket 620 can be formed from metal (e.g., stainless steel, Nitinol) or a polymer (e.g., a relatively stiff polymer such as high-density polyethylene). FIG. 8B shows a front view of the bracket 620. FIG. 8B also shows a bias element 629 which extends across the space 624. The bias element 629 can have a spring force such that when the layers of the strip are placed within the space 624, the bias element 629 presses against one of the layers to maintain contact or proximity between the layers. As discussed further, maintaining proximity between the layers allows one or more motors to move the layers of the strip relative to one another.

FIGS. 9A-B show top and bottom views of the broad sides of a strip 721 in a completely uncoiled state (i.e. flat). FIG. 9C shows a cross sectional view along line DD of FIG. 9A. The strip 721 can correspond to any strip referenced herein, such as strips 421 or 521. In some configurations, FIG. 9A may show the radially inwardly facing bottom side of the strip 721 (e.g., the second side 419 of FIGS. 6A-D) that faces the lumen of the ring formed by the coiling of the strip 721. Likewise, FIG. 9B may show the radially outwardly facing top side of the strip 721 (e.g., the first side 414 of FIGS. 6A-D) that faces away from the lumen of the ring formed by the coiling of the strip 721. It is noted that either of these sides of the strip 721 and/or any other components of an annular body can be coated with a material to lower the coefficient of friction of sliding surfaces. For example, the inner and outer surfaces of the strip 721 can be coated with a thin layer (not illustrated) of polytetrafluoroethylene or other low friction material to decrease the friction between adjacent layers of the strip 721 that slide against one another during the expansion and contraction phases and/or to electrically insulate the strip 721.

A plurality of motors 725A-B are mounted on the bottom side of the strip 721. A bracket, such as bracket 420, 520, or 620, can be attached to the strip 721 near or over the motors 725A-B, for example. The top portion or bottom portion of the bracket can be attached to either of the broadside surfaces of the strip 721 shown in FIGS. 9A-B, such as by welding, riveting, or adhesive (e.g., epoxy). Each of the motors 725A-B is partially housed within a constraint 726. The topside of the strip 721, as shown in FIG. 9B, includes a trench 727. The inside of the trench 727 is a textured surface 728. In particular, FIG. 9C shows that the trench 727 is located on one side of the strip 721 while the motor 725B is mounted on the opposite side of the strip 721. As also shown, the constraint 726 surrounds the motor 725B on three sides while a fourth side of the motor 725B faces, and contacts, the strip 721. When the strip 721 is coiled, the motors 725A-B and the constraint 726 can partially or fully reside within the trench 727. In this way, the motors 725A-B and/or constraint 726 can be a projection feature on one side of the strip 721 while the trench 727 can be a groove on a second side of the strip 721 opposite the first side. This projection feature can be received within the groove and move within the groove as the layers of the strip 721, when coiled into a ring, slide relative to one another. It is noted that various alternative strip embodiments mat not have a trench and/or texture.

The strips 721 includes a first end 747 that is opposite the second end 748 (the ends representing the poles of the long axis of the strip 721). The first end 747 can define at least part of the inner most or outer most layer of a ring while the second end 748 can define at least part of the other of the inner most or outer most layer of a ring. As shown, the motors 725A-B are located at the first end 747 but not at the second end 748. A bracket, examples of which are shown and discussed herein, can be attached to the strip 747 at the first end 747 and not at the second end 748, in some embodiments.

The motor 725B can move within the constraint 726, but the constraint 726 keeps the motor 725B against or at least close to the strip 721. The constraint 726 can be formed from a metal (e.g., stainless steel, Nitinol) or polymer. The constraint 726 can be welded, glued, and/or riveted to the strip 721, preferably around the periphery of the motor 725B to allow the motor 725B enough clearance from the constraint 726 to move within the constraint 726. In some embodiments, the constraint 726 can be understood as a pocket inside of which the motor 725B resides but within which the motor 725B can move and out of which the motor 725b can extend and elongate when electrically activated. It is noted that the motor 725B can brace itself against the constraint 726 (e.g., the bottom of the constraint 726 in particular) so that the motor 725B can apply a force outside of the constraint 726 (opposite of the surface against which the motor 725B is braced) when activated. While motor 725B is described in connection with the constraint 726, any motor referenced herein can similarly be contained and braced by a similar constraint.

Returning to the view of FIG. 9A, it is noted that each of the motors 725A-B extends beyond the respective constraint 726 in which the motor is partially housed. Each motor 725A-B expands and contracts within the constraint 726 to extend a corresponding greater and lesser degree beyond the constraint 726. The electrical conductors 716 electrically connect the anode and cathode terminals of the motors 725A-B to provide controlling signals.

While a plurality of motors 725A-B are shown in the embodiment of FIGS. 9A-B, it will be understood that a single motor or a greater number of motors (e.g., three, four, five, ten, etc.) can alternatively be used. The motors 725A-B are serially arrayed along the length (as opposed to the width) of the strip 721 as shown unrolled. It is noted that various alternative arrangements of motors are shown elsewhere herein.

Figure 10A:
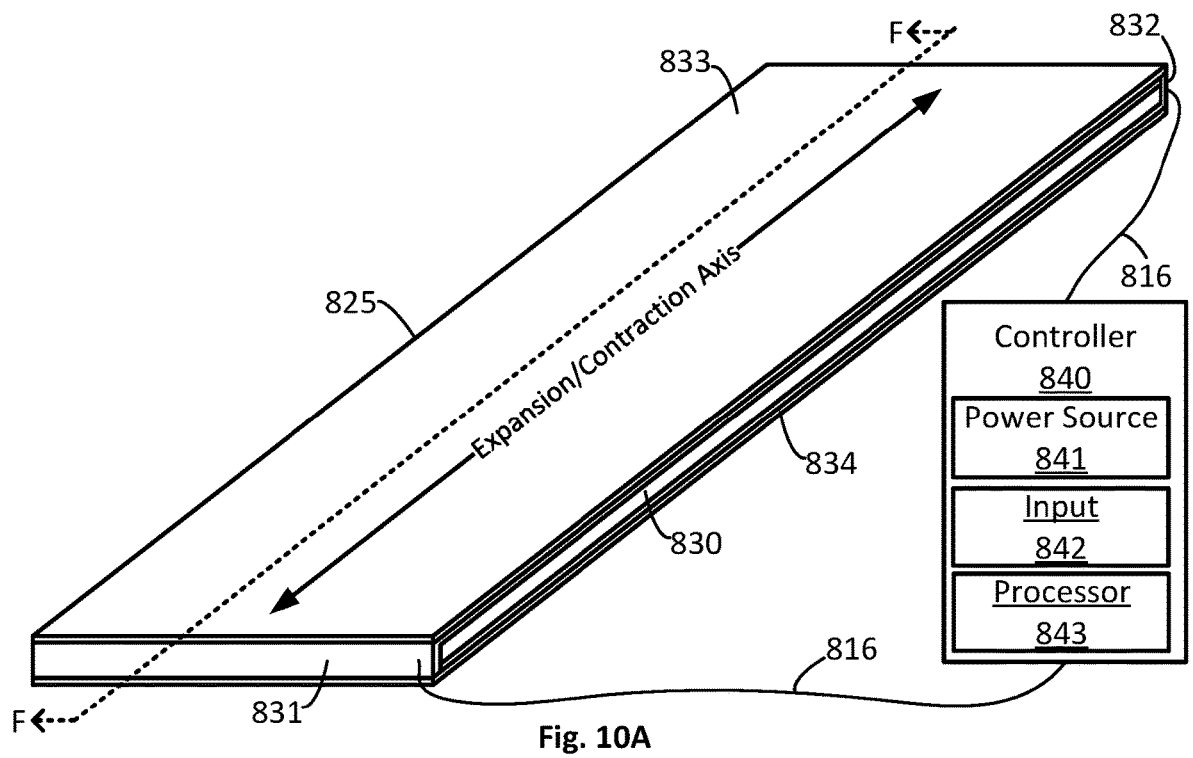
FIGS. 10A-B are schematic and cross sectional views of a motor, respectively.
Figure 10B:
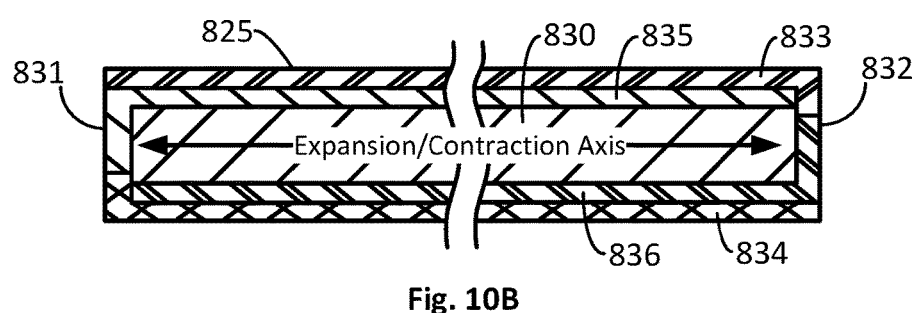
Figure 10C:
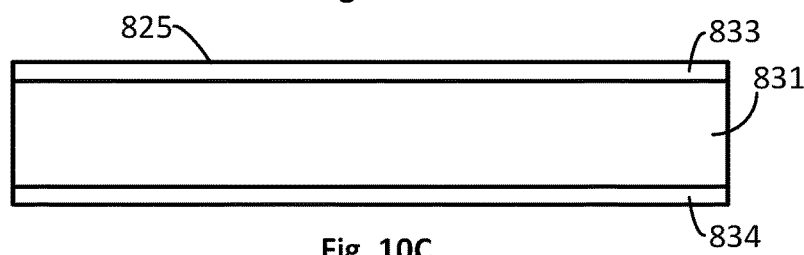
FIGS. 10C-D are end views of the motor of FIGS. 10A-B.
Figure 10D:
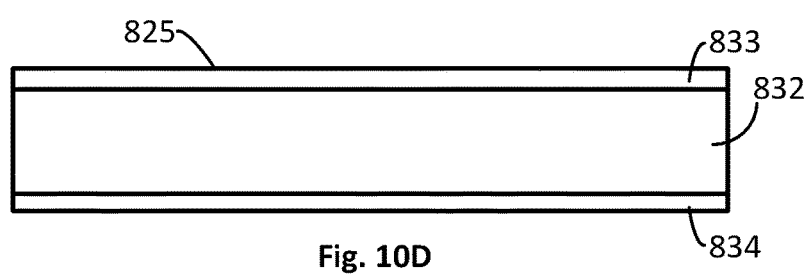

FIG. 10A shows a perspective view of a motor 825. FIG. 10B shows a cross sectional view along line FF of the motor 825 of FIG. 10A. FIG. 10C shows one end of the motor 825 while FIG. 11D shows the opposite end of the motor 825. The motor 825 can correspond to any motor referenced herein, such as for example motors 725A-B.

The motor 825 operates by piezoelectric action whereby an electrical signal applied across the first terminal 831 and the second terminal 832 of the motor 825 generates an electric field across piezoelectric material 830. The first terminal 831 includes a first conductive coating 835 that can extend along a full side (e.g., a top side) of the piezoelectric material 830. The second terminal 832 includes a second conductive coating 836 that can extend along a full side (e.g., a bottom side) of the piezoelectric material 830. The first and second conductive coatings 835, 836 can be formed from a metal, such as gold, copper, or other conductive material, such as conductive epoxy. The opposite major broadsides of the motor 825 are insulated by a first insulative coating 833 and a second insulative coating 834. The first insulative coating 833 and the second insulative coating 834 can be formed from a polymer, such as polyamide.

Piezoelectric materials can include aluminum nitride, barium titanate, gallium phosphate, lanthanum gallium silicate, polyvinylidene fluoride, and lead zirconate titanate, amongst other options. The piezoelectric material 830 includes an elongation/contraction axis along which the piezoelectric material 830 expands or contracts when electrically activated. As indicted, the elongation/contraction axis is orientated along the longitudinal dimension of the rectangular motor 825 to maximize the amount of expansion along this axis. The piezoelectric material 830 has a crystalline structure which causes the piezoelectric material 830 to change dimension. The cells of the crystalline structure function as a dipole due to a charge imbalance. During manufacturing, the piezoelectric material 830 is "polled" by application of a very strong electric field across the piezoelectric material 830 that orientates the dipoles of the cells in a particular direction (e.g., in the direction of the indicated expansion/contraction axis). Removal of the very strong electric field causes some relaxation of the dipole orientation, but during use of the piezoelectric material 830, subsequent application of a less strong signal causes the dipoles to reorientate along the poling direction and/or to cause the dipoles to more precisely align along the poling direction. The dipole reorientation changes the length of the piezoelectric material 830 most dramatically in the dipole direction. In the embodiment of FIGS. 10A-D, the dipole direction can be parallel with the indicated expansion/contraction axis, such that the motor 825 expands and contracts along this axis in response to a signal being applied across the first and second terminals 831, 832. The piezoelectric material 830 may expand and contract in other dimensions/directions upon electrical activation, but such expansion and contraction will be of a much smaller ratio than along its elongation/contraction axis.

The controller 840 can be located, for example, within the handle 7 in the embodiment of FIG. 1. The controller 840 can include a power source 841 (e.g., a battery), an input 842 (e.g., buttons or otherwise corresponding to input 7 of the embodiment of FIG. 1), and/or a processor 843. The controller 840 manages output of control signals to the motor(s) in response to received input to control the motor 825. Multiple conductors 816 can extend from the controller 840 to the first terminal 831 and the second terminal 832 to electrically connect with the first conductive coat 835 and the second conductive coat 836, respectively. The first conductive coat 835 and the second conductive coat 836 can create an electric field between the first conductive coat 835 and the second conductive coat 836 to activate the piezoelectric material 830 located between the first conductive coat 835 and the second conductive coat 836. While one layer of piezoelectric material 830 is shown in the motor 825, various other embodiments can have multiple layers of piezoelectric material that are sandwiched between the first conductive coat 835 and the second conductive coat 836. While the first and second terminals 831, 832 are shown as being on opposite longitudinal ends of the motor 825 to allow the conductors 816 to deliver a differential signal across the piezoelectric material 830, one or both of the first and second terminals 831, 832 may alternatively be provided on one or both of the major broad sides of the motor 825. For example, a first window can be provided through the first insulative coating 833 to provide access to the first conductor layer 835 while a second window can be provided through the second insulative coating 834 to provide access to the second conductor layer 836 for the conductors 816. Regardless of the locations of the first and second terminals 831, 832, a coating of material (e.g., a polymer such as polyurethane) may be provided on the ends of the motor 825 to allow the motor 825 to engage and push off of other components as further discussed herein.

Figure 11A:
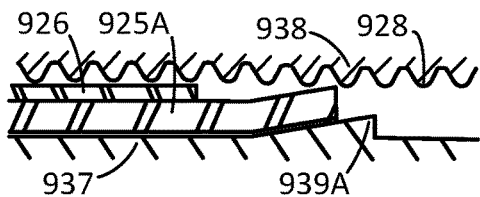
FIGS. 11A-J show steps for sliding layers of a radially adjustable structure.
Figure 11F:
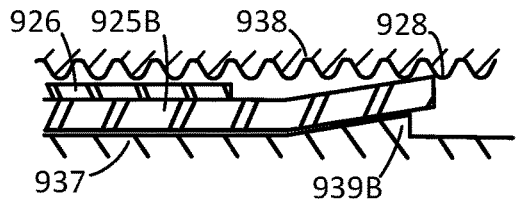
Figure 11B:
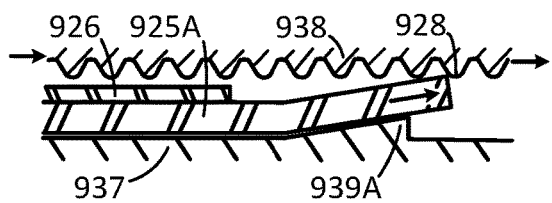
Figure 11G:
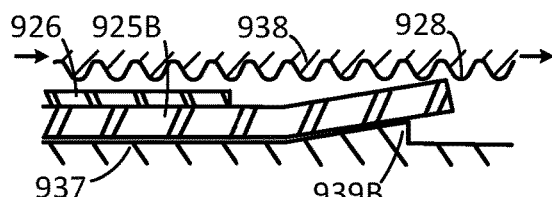
Figure 11C:
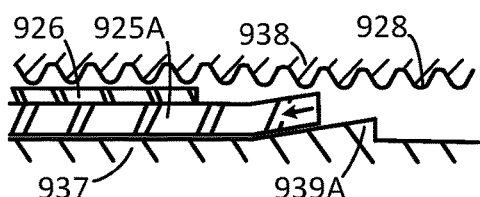
Figure 11H:
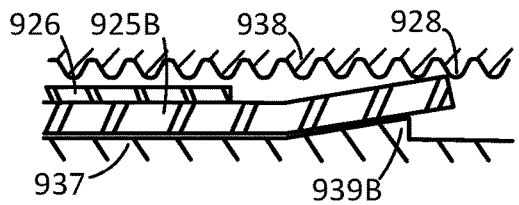
Figure 11D:
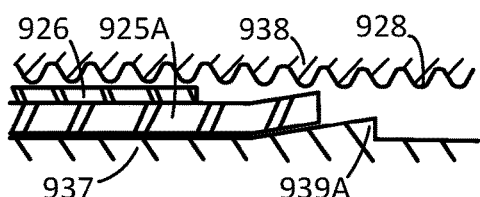

FIGS. 11A-J demonstrate various options for how a motor can move layers of a strip (e.g., any strip referenced herein, coiled for example in the manner of FIGS. 6A-7D, or any other radially adjustable structure) relative to one other to expand and/or contract the radially adjustable structure formed by the strip. For example, FIGS. 11A-J can correspond to the radially adjustable structure 410 of FIGS. 6A-D. Also, FIGS. 11A-E can represent a cross sectional view of line EE of FIG. 9A while FIGS. 11F-J can represent the cross sectional view along line FF of FIG. 9A when the strip 721 is coiled into a ring, but the aspects demonstrated in FIGS. 11A-J are not limited to this embodiment and accordingly can be applied to any aspect or embodiment of a radially adjustable structure. The series of FIGS. 11A-J can represent the states, during expansion and contraction phases, of different motors (e.g., motors 725A, B) positioned at different locations on a coiled strip. Each of FIGS. 11A-E can correspond in time to each of FIGS. 11F-J, respectively. For example, FIGS. 11A and 11F represent different motors at the same point in time, and FIGS. 11B and 11G represent these different motors at another common point in time, etc. The two motors 925A-B are activated to drive the movement cycle of an annular body. Conductors, and well as other components, are omitted from the views of 11A-J for clarity.

Each of FIGS. 11A-11J include a first layer 937 and a second layer 938, which can represent an outermost layer and a second outermost layer (or inner most and second innermost layers), respectively of a coiled strip. One or more brackets (e.g., any bracket referenced herein) can be disposed directly over, or close to, the motors 925A-B to urge the first layer 937 and the second layer 938 close to or against one another to help engagement of the parts, including the motors 925A-B that are sandwiched between the first layer 937 and the second layer 938. Either or both of the motors 925A-B may be at least partially within the space of the bracket when the bracket is directly over the motor. In some embodiments, the motors 925A-B are mounted on the bracket and layer 937 represents part of the bracket while layer 938 represents the outermost or inner most layer of a coiled strip.

The texturing 928 is shown on the side of the second layer 938 that faces the first layer 937. As shown in this embodiment, the texturing 938 includes a series of projections. The texturing 938 can be a series of evenly spaced bumps (e.g., in a pattern resembling a sine wave). The projections can serve as push-off or bracing features for the motors 925A-B. It will be understood that not all embodiments may include such texturing. For example, the surface of the second layer 938 may be flat or otherwise smooth. The constraints 926 are shown as maintaining the position of the motors 925A-B to hold the motors 925A-B against or close to the first layer 937. For reasons that will be demonstrated, motor 925A can be referred to as a "pusher motor" while motor 925B can be referred to as a "bracing motor."

The first layer 937 includes projections 939A-B underneath each of the exposed ends of the motors 925A-B (the exposed ends of the motors 925A-B being those parts of the motors that extend beyond the constraints 926). The projections 939A-B can bias the motors 925A-B to engage the opposite second layer 938. It will be understood that the projections 939A-B are optional and may not be used in all embodiments. For example, the motors 925A-B can rest in an orientated that points the motors 925A-B at the opposite layer 938.

As shown in FIG. 11F, the motor 925B is engaged with one of the projections of the texture 928 of the second layer 938. It is noted that the coiled strip may be biased such that the second layer 938 is biased to move leftward (in the orientation of the view of FIG. 11A) relative to the first layer 937. However, the engagement of the motor 925B with the projection of the texture 928 of the second layer 938 prevents the second layer 938 from moving leftward relative to the first layer 937. In this manner, the motor 925B is serving as a bracing motor in that it maintains the relative positions of the layers 937, 938 of the strip whereby the mechanical bias of the coiled strip would otherwise move layers 937, 938 relative to one another and to a state having less or no stored spring energy (e.g., relaxing by uncoiling). It is noted that the constraints 926 can be, for example, attached to the first layer 937 to anchor a substantial portion of each of the motors 925A-B to the first layer 937, the motors 925A-B only being movable to extend rightward from the constraints 926 (e.g., upon electrical activation) to be exposed for engagement with the second layer 938, amongst other options.

FIGS. 11B and 11G show that motor 925A has been electrically activated and is expanding in length to engage and push a projection of the texture 928 of the second layer 938. As indicated by arrows, this moves the second layer 938 rightward (e.g., clockwise) with respect to the first layer 937. As previously mentioned, the coiled strip is biased such that the second layer 938 would tend to move leftward of the first layer 937 therefore, the activation of the motor 925 pushing the second layer 938 to the right with respect to the first layer 937 is overcoming the mechanical bias of the coiled strip 421 to wind (or further coil) the strip, in the manner of a spring, to store more energy in the coiled strip while also expanding (or alternatively contracting) the annular body formed by the strip. It is noted that the motor 925B is orientated to have a directional orientation that permits texture 928 to slide in one direction over the motor 925B but the motor 925B engages the texture 928 to block motion if the second layer 938 slides in the opposite direction, as shown in FIG. 11H.

Figure 11I:
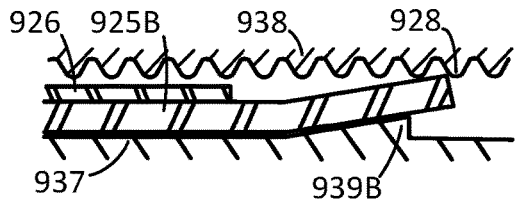

FIGS. 11C and 11H show that motor 925A has been electrically deactivated and is contracting in length to disengage from the previously-pushed projection of the texture 928 of the second layer 938. FIGS. 11D and 11I show that motor 925A has been restored to the same position, relative to the constraint 926 and the first layer 937, as in FIGS. 11A and 11F. While the disengagement of the motor 925A from the projection would otherwise allow the coiled strip to relax and the layers 937, 938 to slide relative to one another to release stored energy, the bracing motor 925B is positioned to engage one of the projections of the texture 928 of the second layer 938. As such, the pushing motor 925A activates to incrementally slide the first and second layers 937, 938 relative to one another while the bracing motor 925B maintains at least some progress of each increment of the pushing motor 925A for each cycle. The expansion and contraction cycle of the motors 925A-B shown in FIGS. 11A-D and 11F-I can be repeated (e.g., thousands of times) for each expansion or contraction cycle of a radially adjustable structure. As such, the diameter of an annular body formed by a coiled strip can be incrementally and progressively expanded or contracted by repeated motor actuation cycles to cause one expansion or contraction phase of a movement cycle of the radially adjustable structure.

Figure 11E:
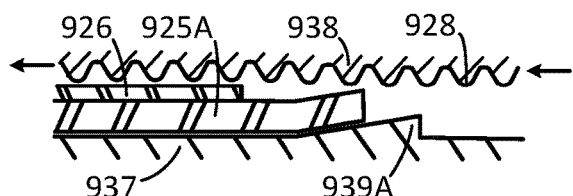
Figure 11J:
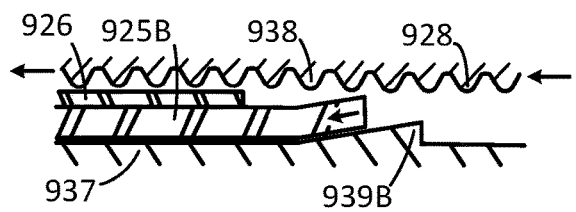

FIGS. 11E and 11J show the activation (or alternatively the deactivation) of the bracing motor 925B. In some embodiments, the bracing motor 925B was held in place through the states corresponding to 11F-I by being electrically activated to be in an expanded state by application of an electrical signal which is then ceased in the state of FIG. 11J to have the bracing motor 925B return to its inactivated (contracted) state. Alternatively, the bracing motor 925B can be of the type that contracts upon electrical activation, such that no signal is supplied to the bracing motor 925B during the states of FIGS. 11A-D and 11F-I but the bracing motor 925B is electrically activated for the state of FIG. 11J to contract. The advantage of this latter option is that no energy is expended to keep the bracing motor 925B in the bracing position during the reciprocation cycles of the pushing motor 925A.

Contraction of the bracing motor 925B in FIG. 11J disengages the bracing motor 925B from the projection of the texture 928 of the second layer 938 to allow the second layer 938 to freely move relative to the first layer 937 as the coiled strip relaxes and release stored energy. Such relaxation of the coiled strip can correspond to the annular body formed by a coiled strip returning to a previous state (e.g., having a particular inner and/or outer diameter). For example, repetition of the cycle shown in FIGS. 11A-D and 11F-I can correspond to expansion of a coiled strip to the state shown in FIGS. 6C-D while release from bracing as shown in FIGS. 11E and 11J can correspond to contraction of the strip to the state shown in FIGS. 6A-B. Alternatively, repetition of the cycle shown in FIGS. 11A-D and 11F-I can correspond to contraction of a coiled strip to the state shown in FIGS. 7A-B while release from bracing as shown in FIGS. 11E and 11J can correspond to expansion of the strip to the state shown in FIGS. 7C-D.

FIGS. 11A-J demonstrate how layers 937, 938 of a coiled strip can be slid relative to each other. Sliding the layers either further coils, or partially uncoils, the strip, depending on the direction of relative sliding. Further, sliding the layers relative to each other either increases the circumference of the ring or decreases the circumference of the ring, depending on the direction of sliding, and correspondingly increases or decreases the diameter of the ring.

It is noted that it may be a single motor that drives the expansion or contraction cycle, such as motor 925A, while another motor or non-motor element (e.g., part of the first layer 937) merely braces to maintain the incremental progress, such as motor 925B or a non-moving structure similar to the projection 939B that projects upward to engage the texture 928 and prevent motion in a particular direction between the layers 937, 938. For example, the projection 939B may be much taller so as to engage the texture 928. It is noted that some radially adjustable structures (or catheters) may have only one motor, or may lack a dedicated bracing motor, by having the motor preform both pushing and bracing. For example, the reciprocation cycle of the motor may act faster than the relaxation action of the spring of the radially adjustable structure (e.g., coiled strip) such that the motor does not need a separate motor to brace between pushing cycles because the motor shortens and elongates before the spring retracts enough to undue the incremental progress of one cycle, and the motor can remain in an elongation configuration to brace when no further expansion (or contraction, as the case may be) of the radially adjustable structure is desired. For example, the motor may cycle at a rate between 500-3,000 hertz.

FIGS. 11A-D represent a reciprocation cycle for the pusher motor 925A, each reciprocation cycle incrementally moving the first and second layers 937, 938 relative to one another such that a plurality of reciprocation cycles add up to move the first and second layers 937, 938 distances relative to each other greater than a single increment of a reciprocation cycle. A reciprocation cycle for a motor refers to either expansion of the motor from an initial state and then contraction back to the initial state, or contraction of the motor from an initial state and then expansion back to the initial state of the motor. Even though each incremental movement may be very small, many reciprocation cycles can be executed within a very short time. For example, motors (including piezoelectric motors) can have very high cycle times, such as 1 Hz-1 KHz. It is noted that the motors 925A-B can be piezoelectric based, but can also be other types of motors, such as those further described herein. As such, moving layers relative to one another to expand an annular body is not limited to piezoelectric motors.

Figure 12A:
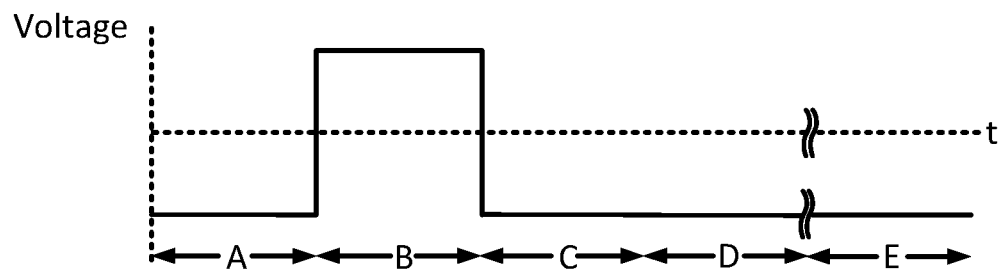
FIGS. 12A-D show electrical command signals for motor activation motor.

FIG. 12A illustrates a signal which can be applied to a motor, such as the pushing motor 925A during the reciprocation cycle shown in FIG. 11A-D. Continuing with this example, the letters A, B, C, D, and E correspond with the phases in time of the FIGS. 11A-E, respectively. In particular, a voltage may only be applied across the pushing motor 925A during a pushing phase "B". FIG. 12C shows a different, but similar, signal that can be applied to the pushing motor 925A (or any other motor) during the reciprocation cycle shown in FIG. 11A-D. While square waves are shown, any types of signals can be delivered to motors, including sine, triangular and sawtooth shapes. The signals may be generated by a programmable or dedicated signal generator of controller 840. Such signals can be delivered to any type of motor referenced herein.

Figure 12B:
Figure 12C:
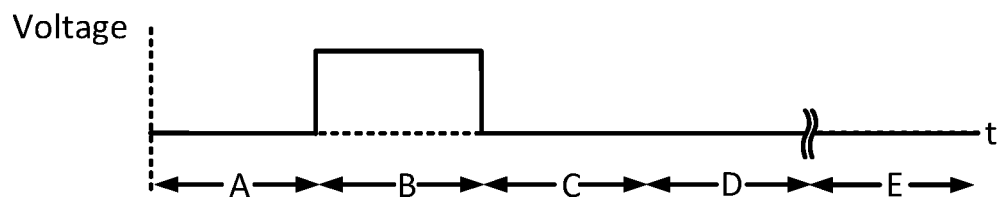
Figure 12D:
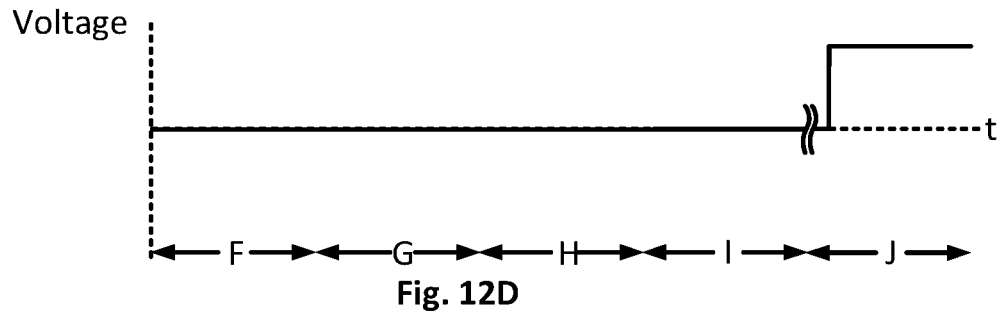

FIG. 12B shows a signal that can be applied to a motor, such as the bracing motor 925B during the reciprocation cycle shown in FIGS. 11F-J. Continuing with this example, the bracing motor 925B can be electrically activated to elongate during each of the phases F, G, H, I and deactivated to shorten during the J phase. FIG. 12D shows a different signal that can be applied to the bracing motor 925B in which the bracing motor is not electrically activated during phases F, G, H, I but is electrically activated to contract during phase J to allow the layers to slide relative to one another as the radially adjustable structure relaxes. The difference between the signals of FIG. 12B, D is that the motor 925B is activated by the signal of FIG. 12B (which in this embodiment expands upon activation) to maintain expansion in phases F-I and is only deactivated to phase J while the motor 925B is activated by the signal of FIG. 12B (which in this embodiment contracts upon activation) only during phase J to contract.

FIGS. 13A-C show different views of a strip 1021, the views similar to those of FIGS. 9A-C, respectively. The embodiment of FIGS. 13A-C can be similar to those shown in, and/or described in connection with, FIGS. 9A-C, except that the motors 1025A-C are shown as arrayed across the width of the strip 1021 instead of serially arranged along its length as in FIGS. 9A-C. As previously described, the multiple motors 1025A-C can work together to alternately push and brace the strip 1021 to drive a radially adjustable structure through expansion and/or contraction phases. For example, motors 925A, C can be pushing motors while motor 925B can be a bracing motor. Alternatively, all motors 925A-C can be pushing and bracing motor that operate with a fast reciprocation cycle. While three motors are shown arrayed across the width of the strip 1021, a greater or lesser number of motors can be provided.

It is noted that the motors 1025A-C are arrayed across the width of the strip 1021 while motors 725A-B of the embodiment of FIGS. 9A-C are arrayed along the length of the strip 721. These concepts can be combined such that a two dimensional array of motors includes X number of columns of motors (arrayed along the length of the strip) and Y number of rows (arrayed along the width of the strip). These motors can still fit partially or fully within the trench 1027 and engage the texture 1028 to function as pushing and bracing motors as described herein.

FIGS. 13A-B also illustrate tabs 1046. The motors 1025A-C are located at the first end 1047 of the strip 1021 while the tabs 1046 are located at the second end 1048 of the strip 1021. While the tabs 1046 are shown on one end of the strip 1021 (the end opposite the end at which the motors 1025A-C are located) in FIGS. 13A-B, tabs 1046 can additionally or alternatively be added to the first end 1047, such as past the motors 1025A-C. The tabs 1046 may be formed from the same material as the strip 1021 or may be formed from a different type of material. The tabs 1046 can be wider than the bracket (e.g., 420, 520, 620) or at least the space (624) within the bracket such that the tabs 1046 engage the side walls of the bracket to prevent the end of the strip 1021 on which the tabs 1046 are placed from slipping out of the bracket. The tabs 1046 can be folded inward while the layers of the strip 1021 are threaded through the space of the bracket during assembly and then projected laterally outward, as shown, after the layers of the strip 1021 have been threaded through the space of the bracket. Alternatively, the tabs 1046 may be added only after the layers of the strip 1021 have been threaded through the space. The tabs 1046 can take different forms and/or can be provided on any other strip.

FIG. 14A shows another alternative embodiment of a strip 1121 in which motors 1125A-E are placed inside constraints structures 1126 such that the first set of motors 1125A-C are pointed in a first direction (e.g., by emerging from the constraints 1126 in the first direction) and a second set of motors 1125D-F are pointed in a second direction opposite that of the first direction (e.g., by emerging from the constraints 1126 in the second direction). Each of the center motors 1125B, F of these first and second sets can be bracing motors while the motors on the lateral sides, specifically motors 1125A, C, D and E can be pushing motors. Because the two sets of motors point in different directions, the motors can be activated and deactivated in the same manner as previously discussed herein to push the layers of the strip 1121 relative to one another when coiled. While some of the previous embodiments pushed the coiling of the strip through one of a contraction or expansion phase and then relied upon the relaxation of the coiled strip to carry out the other of the contraction or expansion phase, pointing motors in opposite directions allows the radially adjustable structure to be actively pushed by motors through each of the contraction and expansion phases. The motors 1125A-F are located at the first end 1147 of the strip 1121 but not on the second end 1148 of the strip 1121.

FIG. 14B shows a strip 1221 having a single motor 1225. The motor 1225 is housed partially within the constraint 1226. The motor 1225 is located on the first end 1247 of the strip 1221 and not on the second end 1248. As discussed preciously, a single motor 1225 can both push and brace instead of relying on multiple motors to separate push and brace functions.

FIGS. 15A-E illustrates an alternative configuration for utilizing expandable motors to move layers of a strip relative to one another. The strip is coiled to include a first layer 1337 and a second layer 1338. The layers can correspond to any of the other layers of a radially adjustable structure. A plurality of motors 1325A-D are mounted on the first layer 1337 (e.g., attached by an epoxy adhesive) and are not attached to the second layers 1338, although the motors 1325A-D may come into contact with the second layer 1338 as further explained. Each of the motors 1325A-D may expand and contract based on application of an electrical signal, such as by being piezoelectric-based or any other type of motor referenced herein.

Figure 15A:
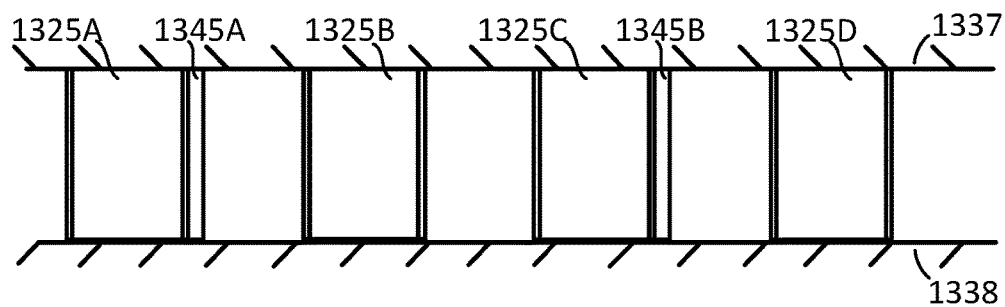
FIGS. 15A-E show steps for sliding layers of a radially adjustable structure.
Figure 15B:
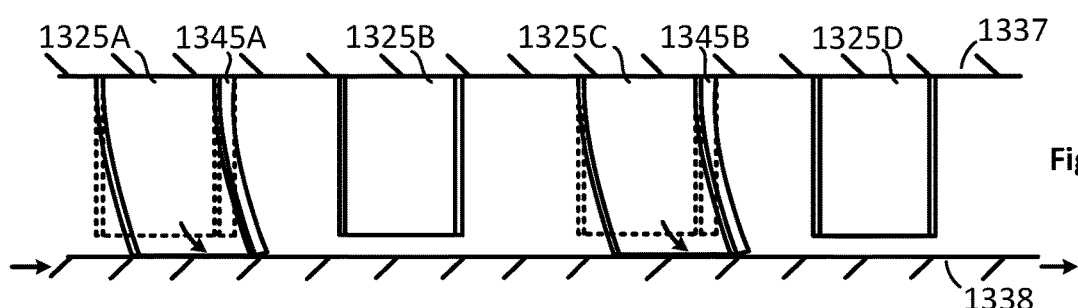
Figure 15C:
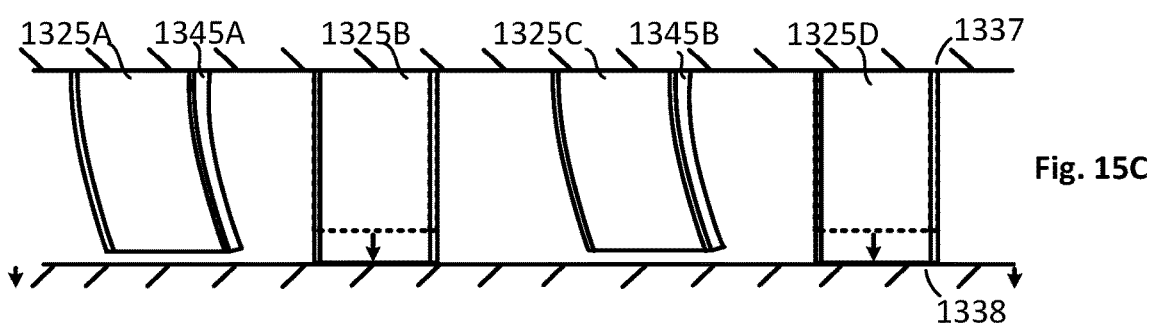
Figure 15D:
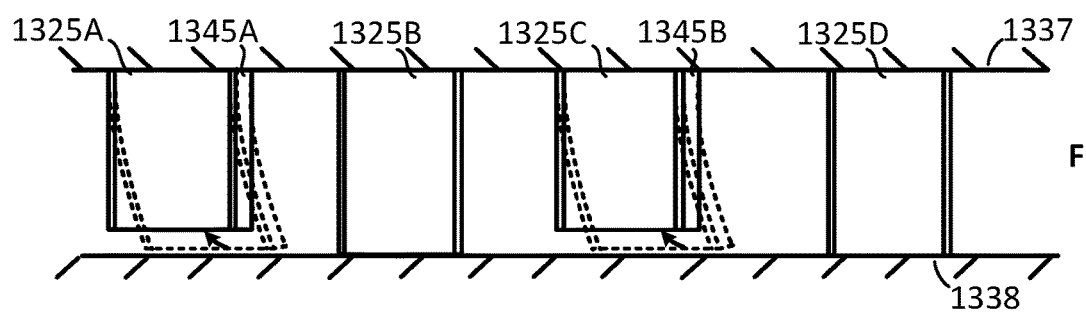
Figure 15E:
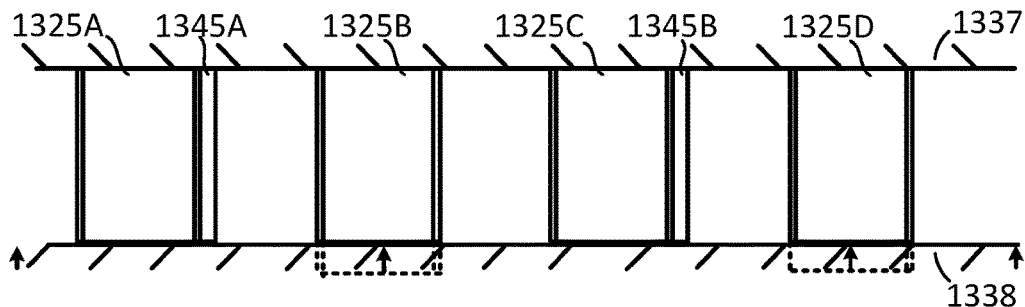

Constraints 1345A-B can be attached (e.g., with adhesive such as epoxy) to a particular side of each of the motors 1325A, C respectively, to cause these motors 1325A, C to bend upon activation as shown in FIG. 15B. As shown in FIG. 15B, motors 1325A, C are activated to expand, and in expanding also curl in the direction on which the constraints 1345A, B are disposed on these motors. The curling action causes the motors 1325A, C to push the second layer 1338 laterally while the longitudinal expansion of the motors 1325A, C engages the second side 1338 to create separation between the layers 1337, 1338. It is the lateral pushing that incrementally moves (e.g., slides) the layers relative to one another to expand or contract a radially adjustable structure as discussed and shown previously. As shown in FIG. 15C, motors 1325B, D can act as bracing motors and activate to engage the second layer 1338. Motor 1325B, D may have a longer longitudinal expansion than motors 1325A, C because motor 1325B, D lack a constraint that otherwise redirects some of the expansion laterally. The activation of motors 1325B, D lifts the second layer 1335 off of motors 1325A, C to allow motor 1325A, C to deactivate and contract as shown in FIG. 15D while motors 1325B, D continue to brace the first layer 1337 relative to the second layer 1338. FIG. 15E shows the deactivation of motors 1325B, D to bring the first layer 1337 closer to the second layer 1338 such that all motors 1325A-D are engaged with the second layer 1338.

FIGS. 15A-E represent a reciprocation cycle of motors 1325 A, C which can be repeated numerous times to incrementally move the first layer 1337 relative to the second layer 1338 to expand and/or contract a radially adjustable structure. The direction of movement can be reversed by providing a second set of motors, similar to motors 1325A,C, except that the side of the motors on which the constraint 1345A-B is placed is reversed such that the second set of motors curl to the left when activated instead of to the right as shown for motors 1325A, C in FIG. 15B. Such motion can reverse the relative sliding of the layers to that as shown in FIG. 15B. In some embodiments, only one or more bending motors (e.g., motors 1325A, C having constraints 1345A, B) are provided on a strip while motors that merely extend straight (e.g., motors 1325B, D), which perform a bracing function, are not included. The bending motors can cycle in a rapid manner as previously explained so that bracing is not needed because the reciprocation repeats before the strip can relax past the incremental pushing progress. It is noted that FIGS. 15A-E demonstrate the use of motors to move layers of a strip that are not textured.

Figure 16A:
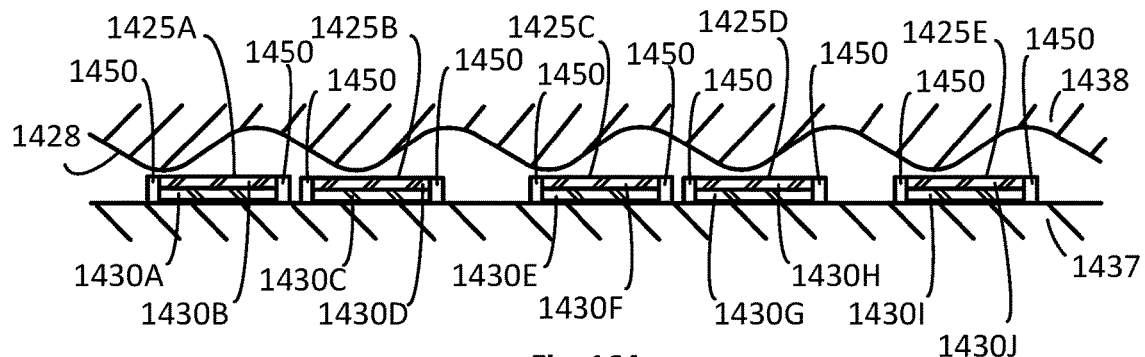
FIGS. 16A-C show steps for sliding layers of a radially adjustable structure.
Figure 16B:
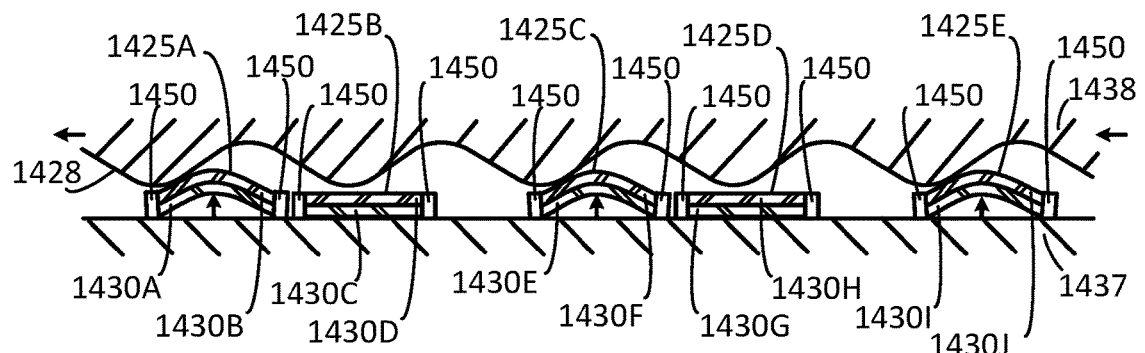
Figure 16C:
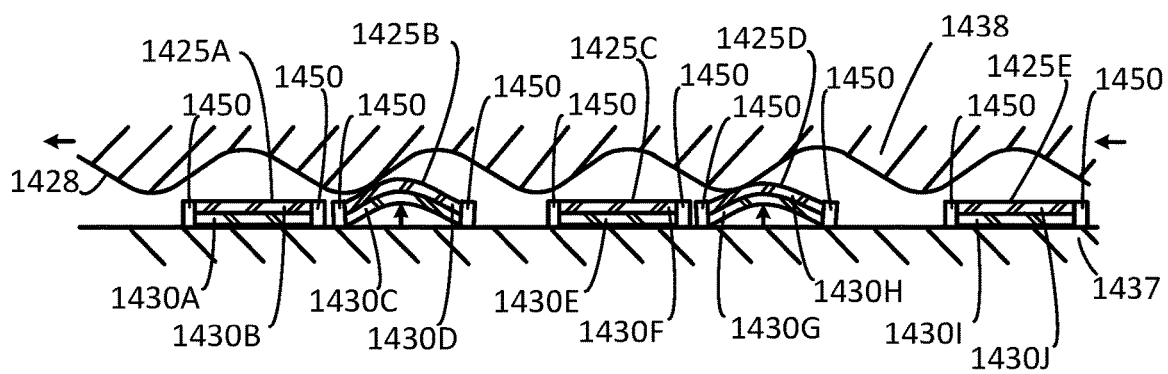

FIGS. 16A-C show an alternative configuration for causing a first layer 1437 to move relative to a second layer 1438. The layers 1437, 1438 can correspond to any adjacent layers of a radially adjustable structure. The embodiment includes a plurality of motors 1425A-E which are mounted (e.g., attached by an adhesive epoxy) on the first layer 1437 and are not directly attached to the second layer 1438. Each of the motors 1425A-E may be piezoelectric motors or any other type of expansion and/or contraction motor referenced herein. The particular embodiment shown includes two layers for each motor. Motor 1425A includes layers 1430A, B. Motor 1425B includes layers 1430C, D. Motor 1425C includes layers 1430E, F. Motor 1425D includes layers 1430G, H. Motor 1425E includes layers 1430G, H. Each motor layer can correspond to a different layer of piezoelectric material polled in a different direction than the other layer of the same motor. In some cases, the top layers 1430B, D, F, H, and J may be active layers that elongate when electrically activated while bottom layers 1430A, C, E, G, I may be constraint layers that are not electrically activated but are attached to the top layers and force the top layers to curl as shown when the top layers expand. Alternatively, the bottom layers 1430A, C, E, G, I may contract when electrically activated simultaneous with the expansion of the top layers such that the layers work together to curl upward toward the second layer 1438.

The motors 1425A-C can be divided into a first group comprising motors 1425A, C, E and a second group comprising motors 1425B and D. These first and second groups of motors can be alternately activated as shown in FIGS. 16B, C. When electrically activated, the motors 1425A-E can project upward to engage the textured surface 1428 of the second layer 1438. The motors 1425A-E push against the slopes of the textured surface 1428 such that the motors force the second layer 1438 to slide relative to the first layer 1437. The first and second groups of motors, and optionally more groups, can be positioned staggered relative to each other and positioned relative to the pattern of the textured surface 1428 such that at least one of groups of motors is always aligned with a downslope of the textured surface 1428 so that activation of the group pushes the layers of the strip relative to one another. The layers can be moved in the opposite direction by pushing against the opposite downslope as that shown in FIGS. 16B, C.

Figure 17A:
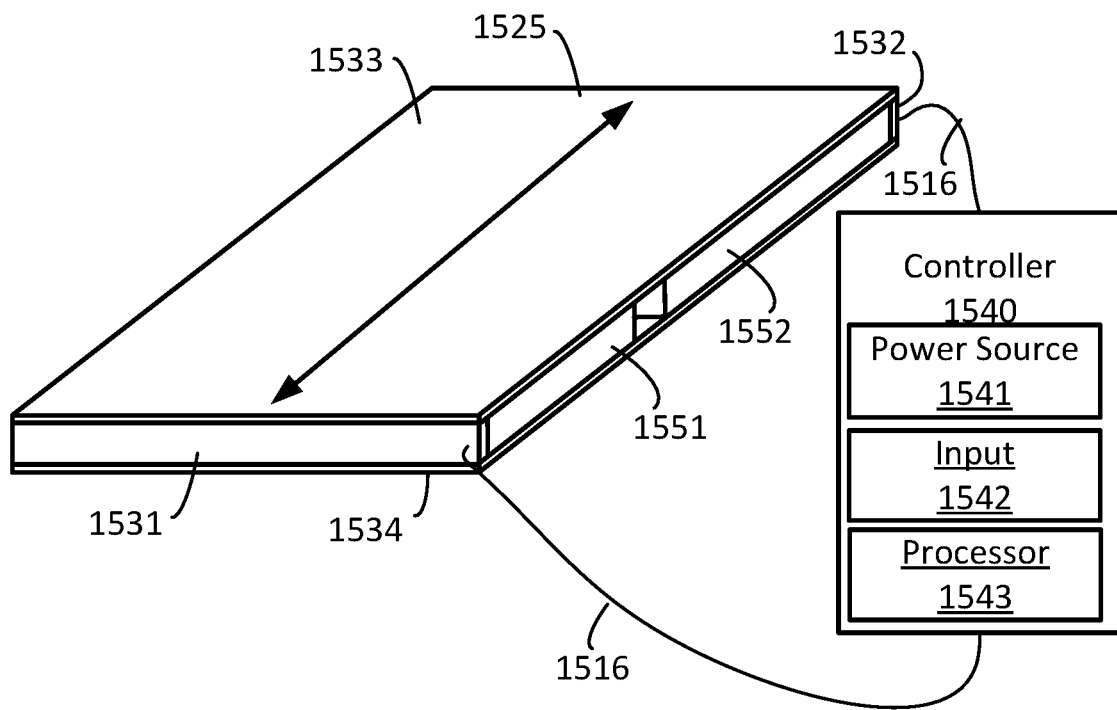
FIGS. 17A, B-C are schematic and detailed views of a motor, respectively.
Figure 17B:
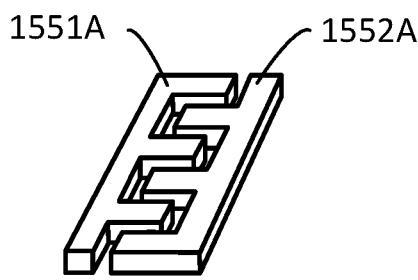
Figure 17C:
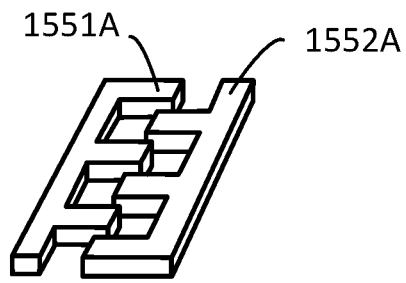

FIGS. 17A-C shows an alternative motor design. This motor design can be used in the radially adjustable structures referenced herein, and can substitute for the piezoelectric-based motors referenced herein. The motor 1525 can be an electrostatic motor or an electromagnet motor. A top side of the motor 1525 is defined by a first insulative coating 1533 and a bottom side of the motor 1525 is defined by a second insulative coating 1534. The motor includes a first terminal 1531 and a second terminal 1532. The first terminal 1531 is electrically connected to a first pole 1551. The second terminal 1532 is electrically connected to a second pole 1552. A space exists between the first pole 1551 and the second pole 1552. The first terminal 1531 and the second terminal 1532 are electrically connected via separate channels to the controller 1540.

The controller 1540 can include a power source 1541 (e.g., a battery), an input 1542 (e.g., buttons or otherwise corresponding to input 7 of the embodiment of FIG. 1), and/or a processor 1543. The controller 1540 manages output of control signals to the motor(s) 1525 in response to received input. Multiple conductors 1516 can extend from the controller 1540 to the first terminal 1531 and the second terminal 1532, respectively, to electrically connect with the first pole 1551 in the second pole 1552, respectively. The controller 1540 can supply one or more signals across the first pole 1551 and the second pole 1552 to create electric fields of the same polarity about the first pole 1551 and the second pole 1552 that repulse each other sufficient to move the first pole 1551 away from the second pole 1552 to elongate the motor 1525. Additionally or alternatively, the controller 1540 can supply one or more signals to the first pole 1551 and the second pole 1552 to create electric fields of opposite polarity from the first pole 1551 and the second pole 1552 that attract each other sufficient to move the first pole 1551 toward from the second pole 1552 to elongate the motor 1525. Expansion and/or contraction of reciprocation cycles can be performed by the motor 1525 based on these signals. In the case of an electrostatic design, charges can be built up from the signals on each of the first pole 1551 and the second pole 1552 to generate attractive or repulsive fields. In the case of an electromagnetic design, magnetic fields can be generated within each of the first pole 1551 and the second pole 1552 by sinusoidal signals run through helically wound conductors within the first pole 1551 and the second pole 1552 to generate attractive or repulsive electromagnetic fields.

FIGS. 17B-C illustrate possible configurations for the first pole 1551 and the second pole 1552. FIGS. 17B-C show how a first pole 1551A can move relative to a second pole 1552B, facilitated by intermeshed prongs of the first pole 1551A and the second pole 1552A.

While FIGS. 6A-17C disclosed various ways to enable expansion and/or contraction of a part of a medical device with a radially adjustable structure, FIGS. 18A-24 show several configurations and applications for such expandable and/or contractible features.

Figure 18A:
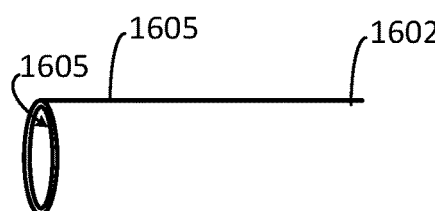
FIGS. 18A-H are a series of perspective views of a catheter capturing an object.
Figure 18B:
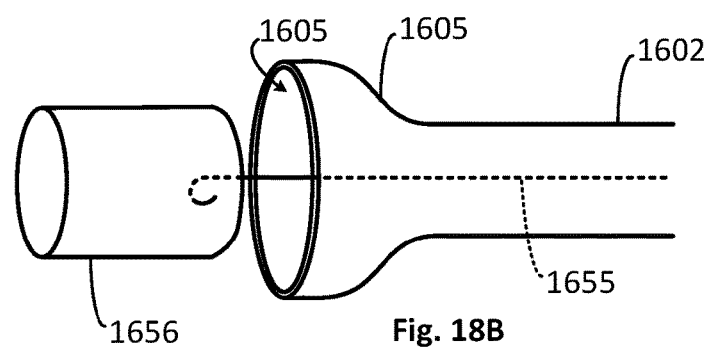

FIG. 18A-18H shows a catheter 1602 having a distal section 1605. The catheter 1602 can correspond with any catheter referenced herein, such as catheter 2. Catheter 1602 is in the form of an elongated tube having a lumen 1615. At least in the form of a tube, the catheter 1602 can be a round body. One or more radially adjustable structures can be mounted on the catheter 1602 in any manner referenced herein (e.g., embedded in the catheter wall in the manner of FIG. 2A-D). FIG. 18A shows the distal section 1605 of the catheter 1602 as having a uniform outer profile. FIG. 18B shows a funnel having been formed from the lumen 1605 in the distal section 1605 by a radially adjustable structure.

FIG. 18B shows object 1656 distal of the catheter 1602. The catheter 1602 can be used to remove the object 1656 from within the body. The object 1656 can be a natural object such as body tissue or material that otherwise forms within the body. The object 1656 can be an artificial object such as an implantable component, stent, valve, filter, support, drain, or any artificial element introduced into the body. While a generally cylindrical object 1656 is shown, it will be understood that this can represent any number of shapes, including non-cylindrical shapes. It is noted that the object 1656 may have been deployed from the distal section of the lumen 1605, such as in the case of the object 1656 being a stent, filter, valve, graft or other medical device.

The object 1656 is attached to an attachment tool 1655. The attachment tool 1655 can include a hook, snare, grasping element, spear, or any other mechanism by which the object 1656 can be secured. A proximal section of the attachment tool 1655 can extend through one of the ports 8 shown in FIG. 1. The attachment tool 1615 may be advanced distally until it engages attached to the object 1656. Alternatively, the attachment tool 1615 may be advanced distally beyond the distal tip of the catheter 1602 with the object 1656 already attached to the attachment tool 1615. The attachment tool 1655 can draw the object 1656 proximally toward the lumen 1605 and/or the catheter 1602 can be advanced distantly towards the object 1656 to close the distance between the catheter 1602 and the object 1656. As an alternative to an attachment tool, or in combination with the attachment tool 1655, aspiration through the lumen 1615 can be provided. In other words, fluid can be drawn through the lumen 1615 from the proximal section of the catheter (e.g., with a pump or syringe connected to one of the ports 8 shown in FIG. 1) to suck the object 1656 into the lumen 1615 and optionally out the proximal section of the catheter 1602.

Figure 18C:
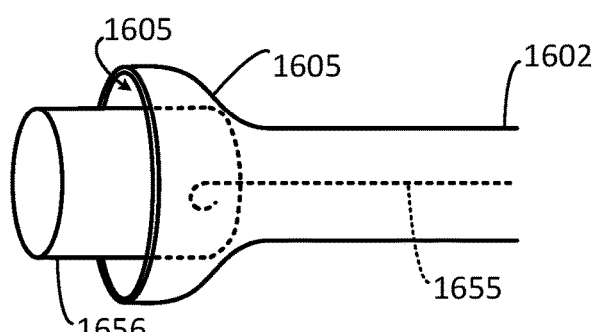
Figure 18D:
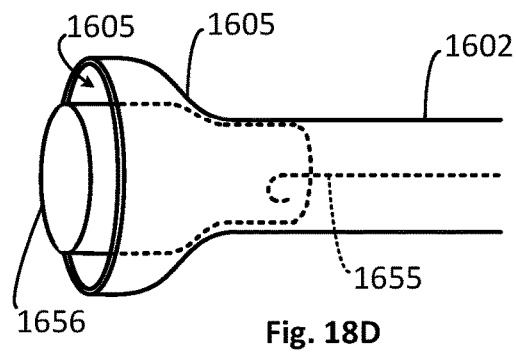
Figure 18E:
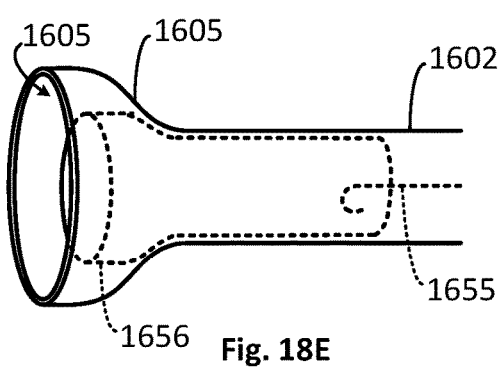
Figure 18F:
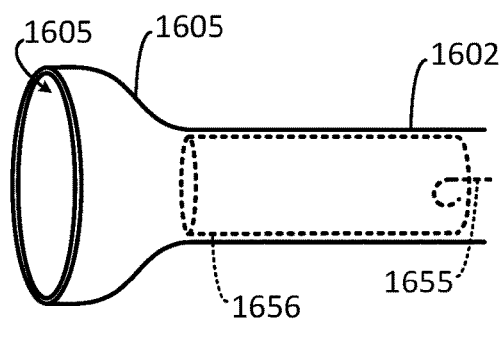
Figure 18G:
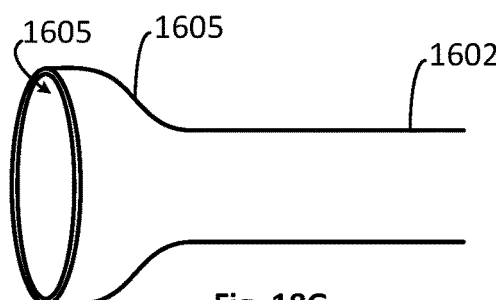
Figure 18H:
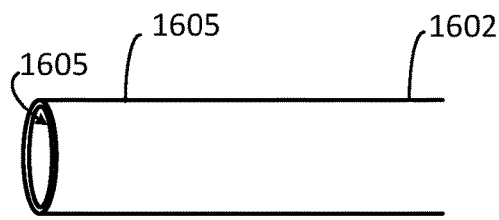

FIG. 18C shows the object 1656 having entered the funnel of the lumen 1605. It is noted that the funnel 1605 has a larger inner diameter distally and a smaller dinner diameter proximally. As shown in FIG. 18D, this narrowing of the lumen 1605 forces the object 1656 to have a smaller profile as the object 1656 is moved within the lumen 1605 proximally and/or the catheter 1605 is moved distally with respect to the object 1656. FIG. 18B shows the object 1656 having been moved further into the lumen 1605, the outer profile of the object 1656 being reduced. FIG. 18F shows the profile of the object 1656 having been reduced to the inner diameter of the non-funnel portion of the lumen 1605. FIG. 18G shows that the object 1656 has been moved through the lumen 1605 to be cleared from the lumen 1605 and catheter 1602 (e.g., removed from one of the ports 8 of FIG. 1). FIG. 18H shows the funnel having been collapsed by contraction of the radially adjustable structure disposed in the distal section 1605 of the catheter 1602. This reduces the profile of the catheter 1602 to facilitate withdrawal of the distal section 1605 of the catheter 1602 from the body.

The catheter 1602 only underwent one movement cycle, comprising an expansion phase (FIGS. 18A-C) and a contraction phase (FIGS. 18G-H) for remove of the object 1656, and the associated radially adjustable structure likewise only undergoes one cycle of expansion and then contraction. In some alternative embodiments, a catheter can undergo multiple movement cycles when capturing one object, as shown in FIGS. 19A-F.

Figure 19A:
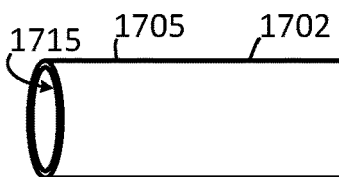
FIGS. 19A-J are a series of perspective views of a catheter capturing an object.
Figure 19B:
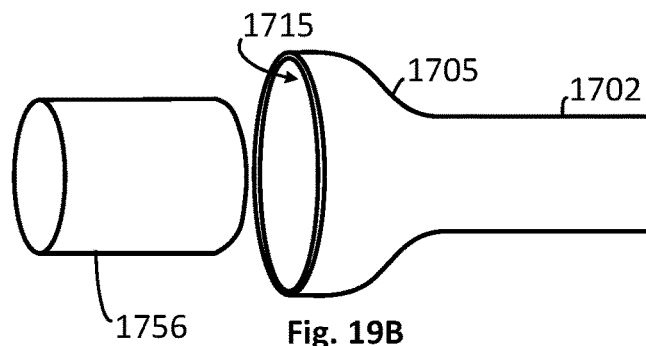
Figure 19C:
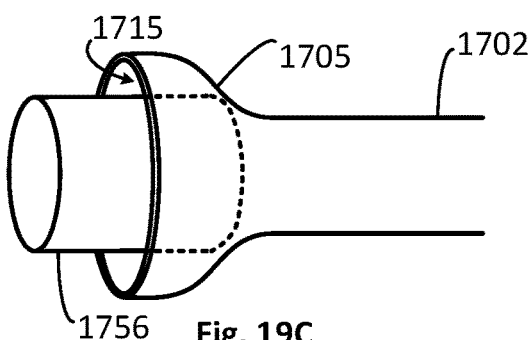
Figure 19D:
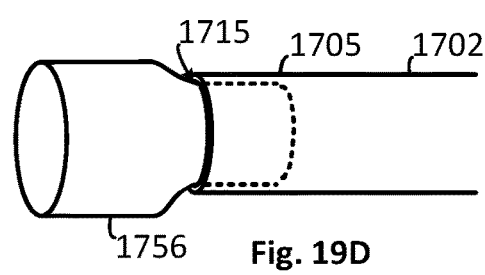
Figure 19E:
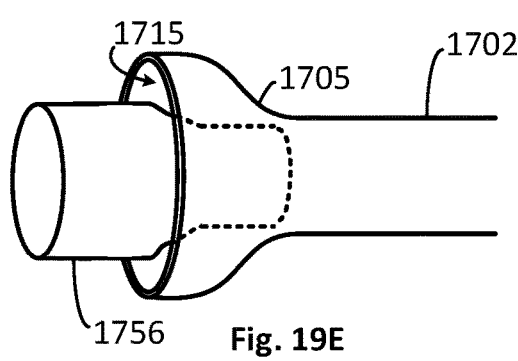
Figure 19F:
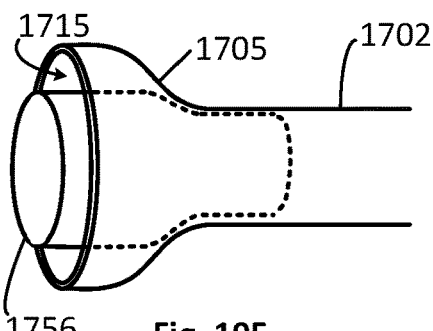
Figure 19G:
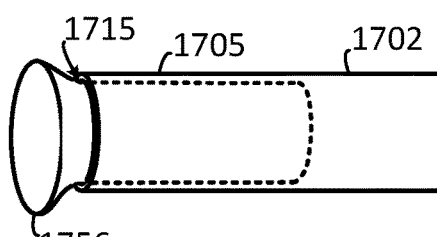
Figure 19H:
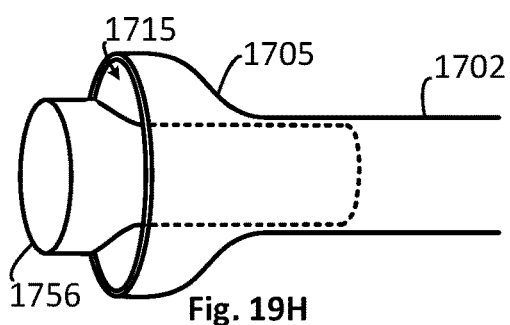
Figure 19I:
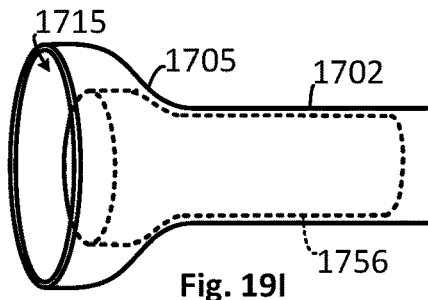
Figure 19J:
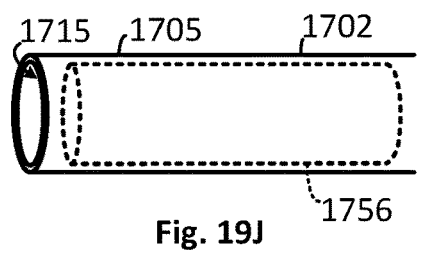

FIGS. 19A-F show a sequence of a catheter 1702 having a distal section 1705 and a lumen 1715 capture an object 1756. The catheter 1702 can be similar to any catheter referenced herein. For example, the catheter 1702 can include a radially adjustable structure embedded within the distal section 1705 to form a funnel shape as shown in FIG. 19B. The object 1756 can be similar to any object referenced herein, such as object 1656. While an attachment tool is not shown in FIGS. 19A-F, an attachment tool can be used to control the object 1756 as with the demonstration shown in FIGS. 18A-H. As described in connection with FIGS. 18A-H, aspiration can be provided through the lumen 1715 to pull the object 1756 into the lumen 1715. It is noted that the aspiration may not have enough power to force the object 1756 to have a smaller outer profile as the object encounters the funnel of the lumen 1715. Therefore, when the object 1756 encounters the funnel of the lumen 1715, as shown in FIG. 19C, the radially adjustable structure on the distal section 1705 can contract to collapse the funnel around the object 1756 to force (e.g., compact) the object 1756 into a smaller profile as shown in FIG. 19D. The funnel can then be re-expanded as shown in FIG. 19E. The now partially compacted object 1756 can then be further drawn into the lumen 1715 as the funnel of the lumen 1715 is formed once again. The process of expanding the funnel and collapsing the funnel to incrementally reduce the profile of the object 1756 is further shown in FIGS. 19G-I until the object 1756 is entirely contained within the lumen 1715 as shown in FIG. 19J. As such, the repeated expansion and contraction of the lumen 1715 can serve to repeatedly reduce the outer profile of sections of the object 1715 until the object can be entirely accommodated within an unexpanded portion of the lumen 1715. It is noted that FIGS. 19A-J represent multiple movement cycles of the catheter 1702, and multiple expansion and contraction phases of the catheter 1702 and the radially adjustable structure mounted thereon. For example, FIGS. 19A-B can represent an expansion phase, FIGS. 19C-D can represent a contraction phase, FIGS. 19D-E can represent another expansion phase, FIGS. 19F-G can represent another contraction phase, FIGS. 19G-H can represent another expansion phase, and FIGS. 19I-J can represent another contraction phase. These phases can be driven by one or more motors and supported by one or more radially adjustable structures.

Figure 20A:
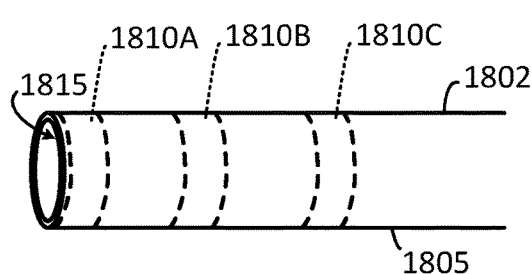
FIGS. 20A-F are perspective views of a medical device undergoing radial change.
Figure 20B:
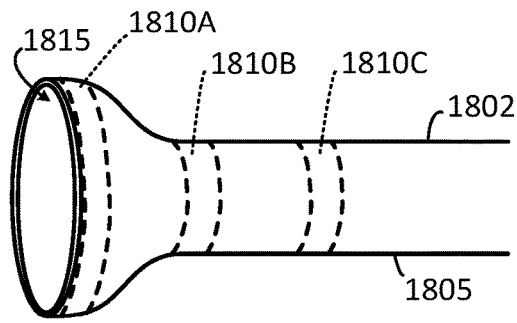
Figure 20C:
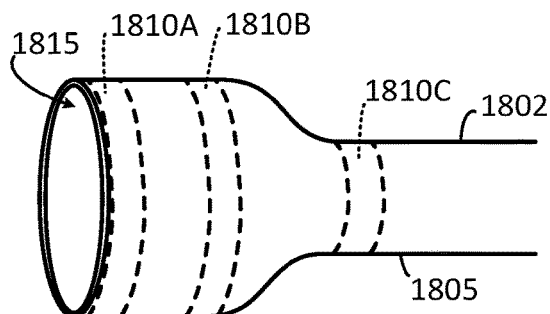

FIGS. 20A-C show an embodiment of a catheter 1802 having multiple radially adjustable structures 1810A-C located within the distal section 1805 of the catheter 1802. The radially adjustable structures 1810A-C are arrayed along the distal section 1805. The radially adjustable structures 1810A-C are not in contact with each other and have spaces therebetween. Each of the radially adjustable structures 1810A-C can be independently controllable such that each can be selectively expanded or contracted. The radially adjustable structures 1810A-C can be of any type referenced herein and contained in the catheter 1802 in any way referenced herein.

Figure 20D:
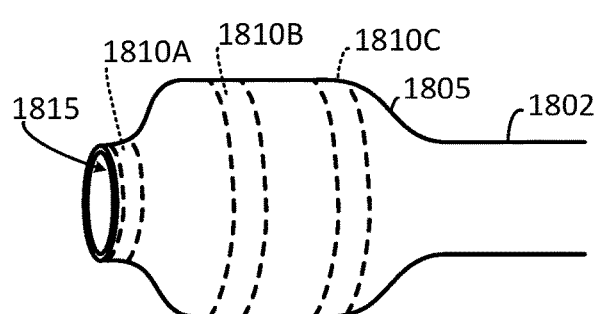
Figure 20E:
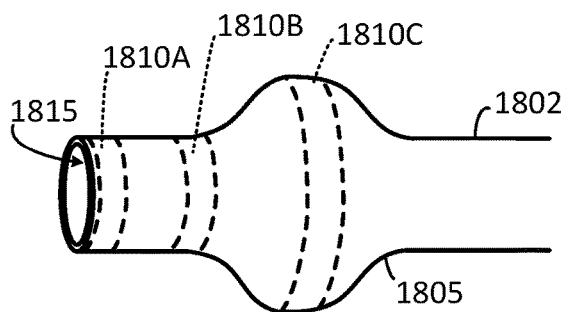
Figure 20F:
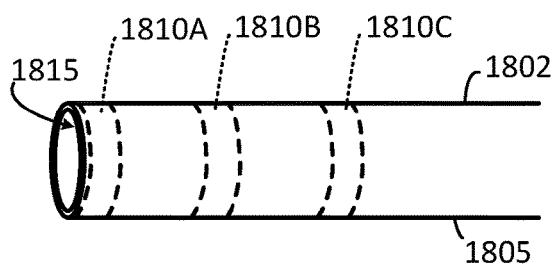

As shown in FIG. 20B, expansion of the distal most radially adjustable structure 1810A forms a funnel. As shown in FIG. 20C, expansion of the second distal most radially adjustable structure 1810B forms a deeper funnel (e.g., longer along the longitudinal axis of the catheter 1802 as compared to the funnel of FIG. 20B). As shown in FIG. 20D, the radially adjustable structure 1810A has contracted down to its original state while radially adjustable structure 1810C has expanded. FIG. 20E shows that the radially adjustable structure 1810B has contracted back to its original state while radially adjustable structure 1810C remains expanded. FIG. 20F shows all of the radially adjustable structures 1810A-C as having been contracted down to their original states of FIG. 20A. As such, FIGS. 20A-F show that waves of expansion and contraction (as well as a bulge) can be propagated along the length of the catheter 1802 by selective expansion and contraction of multiple radially adjustable structures 1810A-C. Such action can be thought of as gulping and/or swallowing of objects through the lumen 1815 to be removed by the catheter 1802. In this manner, objects are accepted into the lumen 1815 and moved through at least the distal section 1805 of the catheter 1802. It is noted that adjacent radially adjustable structures 1810A-C can be in different phases of expansion and contraction of the wave pattern (e.g., both radially adjustable structures 1810A, B are expanded in FIG. 20C while radially adjustable structures 1810B, C expanded in FIG. 20D). It is noted that the selective expansion of different radially adjustable structures 1810A-C need not be for the purpose of capturing an object, and/or need not be at the distal section 1805 of the catheter 1802 so as to form a funnel. For example, the profile of the distal tip of the catheter 1802 may be unaffected by expansion of radially adjustable structures 1810A-C.

Figure 21A:
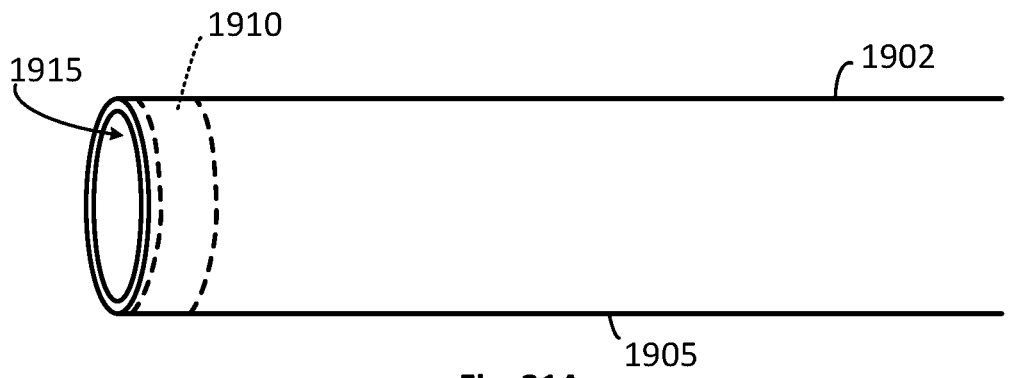
FIGS. 21A-C are perspective views of a medical device undergoing radial change.
Figure 21B:
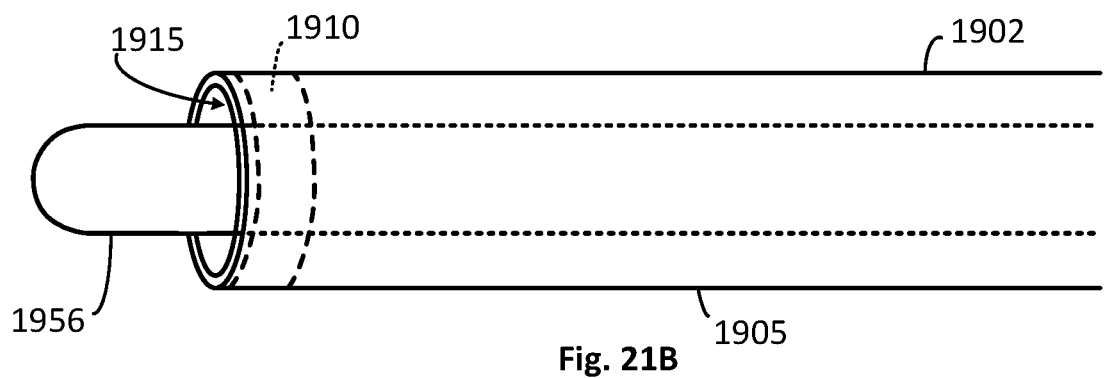
Figure 21C:
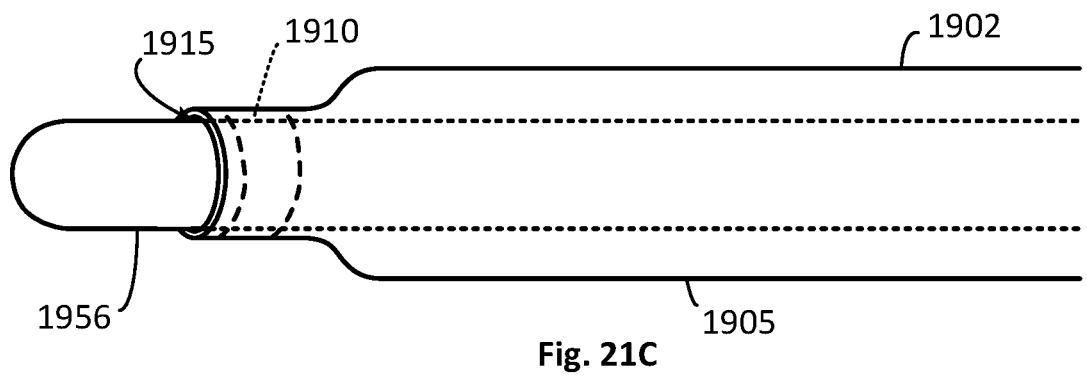

FIGS. 21A-C show an embodiment of a catheter 1902 that can grasp an object through contraction of one or more radially adjustable structures. The distal section 1905 of the catheter 1902 includes at least one radially adjustable structure 1910, which can be of any type referenced herein, mounted in any manner referenced herein. While the radially adjustable structure 1910 is shown very close to the distal tip of the catheter 1902, the radially adjustable structure 1910 can be anywhere along the length of the catheter 1902, and in some cases multiple independently controllable radially adjustable structure can be arrayed along the catheter 1902 (e.g., similar to the embodiment of FIG. 20A-F). As shown in FIG. 21B, a second catheter 1956 can be introduced to the lumen 1915 of the catheter 1902. The second catheter 1956 can be any type of catheter, such as a guide wire, an implant delivery device, a monitoring device, and/or a therapy delivery device. The second catheter 1956 can enter the lumen 1915 from the proximal direction (e.g., through a port of a user handle) or from the distal direction (e.g., through the distal terminus of the lumen 1915). As shown in FIG. 21B, the second catheter 1956 can be extended distally of the catheter 1902 or otherwise traverse the radially adjustable structure 1910. As shown in FIG. 21C, the radially adjustable structure 1910 can be caused to contract to decrease the inner diameter of the lumen 1915. The contraction of the lumen 1915 squeezes around the exterior of the second catheter 1956 to grasp the second catheter 1956, optionally fixing the distal section 1905 of the catheter 1902 to the distal section of the second catheter 1956. Manipulation of either of the catheter 1902 for the second catheter 1956 also manipulates the other such that advancement or retraction of the catheter 1902 also advances or retracts the second catheter 1956 and vice versa. Such grasping can be used to remove the second catheter 1956 from the body or remove any other object, natural or artificial, from the body by first squeezing the object to secure the object and then pulling the object from the body with the catheter 1902.

Figure 22A:
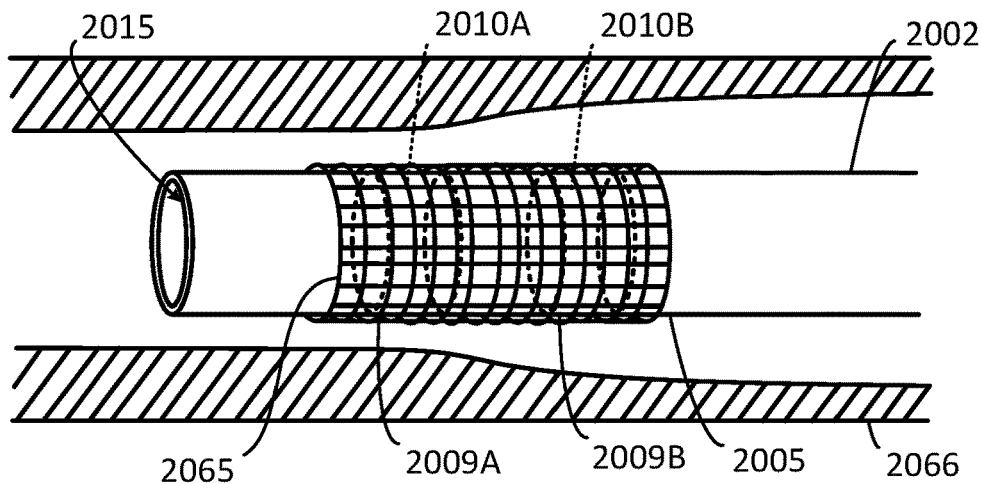
FIGS. 22A-C are perspective views of a catheter deploying a medical device.
Figure 22B:
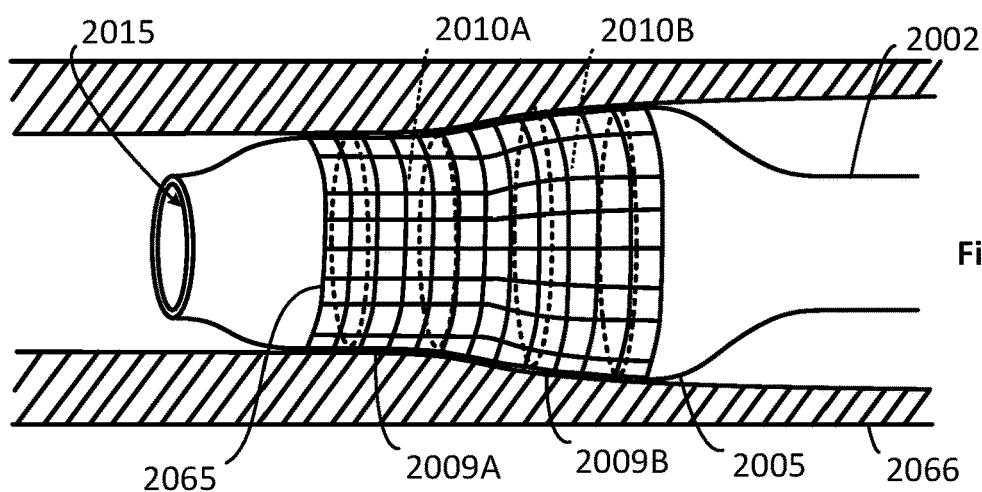
Figure 22C:
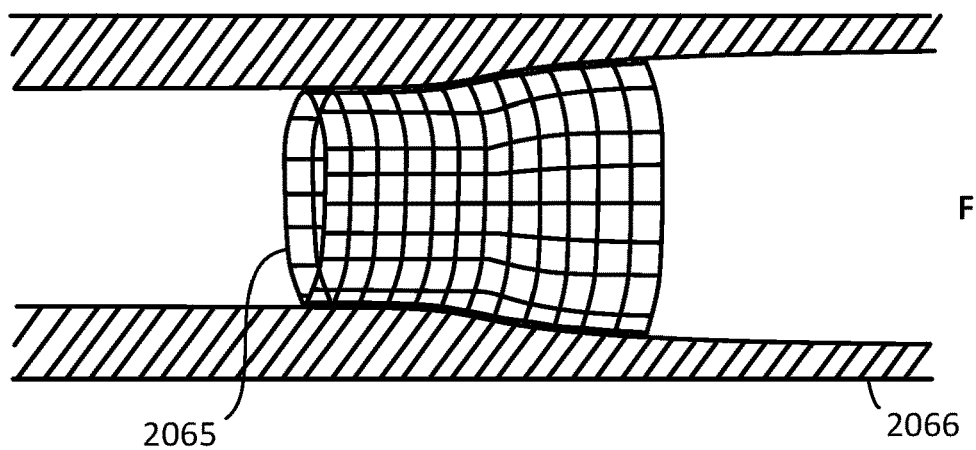

FIGS. 22A-C show how an expandable catheter 2002 can be used to deliver a stent or other implant. A catheter 2002 is introduced into a vessel 2066. The vessel 2066 can be a blood circulatory pathway, an air pathway, a digestive pathway, or any other pathway within the body. Vessel 2066 includes a taper such that the inner diameter of the vessel 2066 changes along its length. A doctor may desire to implant stent 2065 (or other implant) in the vessel 2066 but the change in diameter of the vessel may be challenging for devices that are only expandable to a consistent diameter, such as a balloon. As discussed previously, one advantage of multiple radially adjustable structures is that different sections of the catheter can be expanded or contracted to different sizes at the same time. This may be advantageous when placing an implantable component in a vessel or other anatomical area having different dimensions. Being that the radially adjustable structures are selectively expandable and contractable, the size of the catheter can be dynamically changed as needed along the length of the catheter, as demonstrated by FIGS. 22A-C. The catheter 2002 may be radiopaque so that the doctor can visualize the expanded size(s). Although the catheter 2002 includes a lumen 2015, the lumen 2015 may not be present in all embodiments, such that the catheter 2002 is sealed at the distal tip.

A stent 2065 is mounted around the distal section 2005 of the catheter 2002. Although a stent 2065 is shown, the stent 2065 can represent any type of implant, such as a valve, a filter, or a graft, among other options. Underneath the stent 2065 are multiple, spaced apart radially adjustable structures 2010A-B mounted on the catheter 2002. The radially adjustable structures 2010A-B can be of any type referenced herein, and can be mounted on the catheter 2002 in any manner referenced herein. These arrayed radially adjustable structures 2010A-B can be aligned with different portions of the vessel 2066 having different inner diameters. The radially adjustable structures 2010A-B can be expanded by different amounts such that the outer diameter of the catheter 2002 is increased to different sizes along different longitudinal sections corresponding to the different radially adjustable structures 2010A-B. For example, each of the radially adjustable structures 2010A-B can be expanded to approximately the inner diameter of the portion of the vessel 2066 in which the respective radially adjustable structure resides during expansion to anchor the stent 2065 in the vessel 2066. As shown in FIG. 22B, this can result in implantation of the stent 2052 have different diameters along different longitudinal sections corresponding to different diameters of the vessel 2066 in which it is implanted to best fit the stent 2065 to the native profile of the vessel 2066.

As shown in FIG. 22C, the radially adjustable structures 2010A-B can be contracted to decrease the outer diameter of the distal section 2005 while leaving the stent 2065 in its expanded state, and the catheter 2002 can be withdrawn to leave the stent 2065 in the vessel 2066. While multiple radially adjustable structures 2010A-B are used to deploy stent 2065, a single radially adjustable structure may instead be provided on the catheter 2002 and used for deployment. In some embodiments, multiple stents or other implants can be arrayed along the length of the catheter 2002 and multiple radially adjustable structures mounted on the catheter 2002, respectively underneath the multiple stents (e.g., one or multiple radially adjustable structure for each stent), can be selectively expanded to expand and deploy the stents. In some embodiments, a catheter deploys an implant or other device mounted around the catheter, not in part by the catheter expanding as in FIGS. 22A-B, but rather by the catheter contracting from an original state to loosen the implant mounted around the catheter (similar to FIGS. 22B-C). In some embodiments, the catheter 2002 or other medical device disclosed herein, with or without stent, can be expanded to engage plaque or other material or tissue to perform angioplasty within a vessel. Radial expansion as disclosed herein can push or compact tissue, such as plaque or blood clots, to improve the patency of a vessel.

Figure 23A:
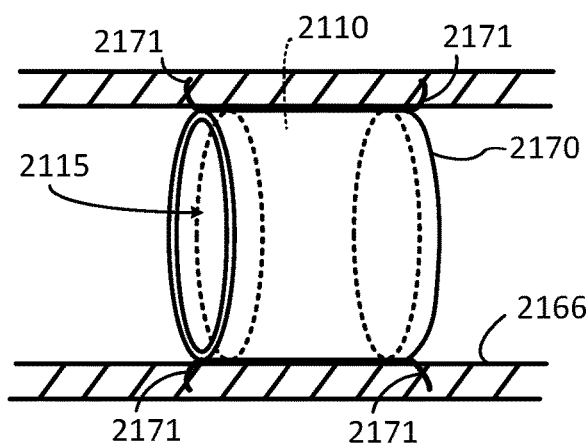
FIGS. 23A-C are perspective views of an implant undergoing using radial change.
Figure 23B:
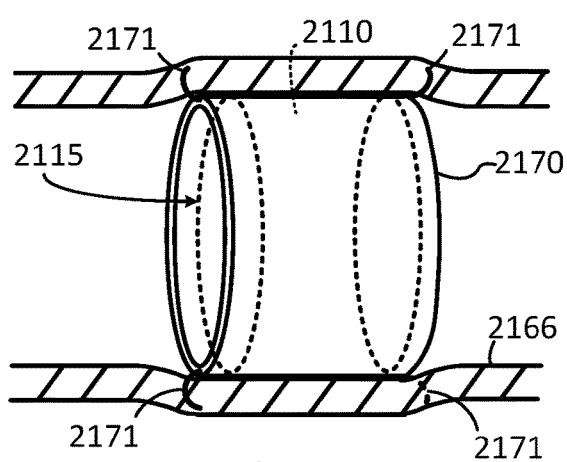
Figure 23C:
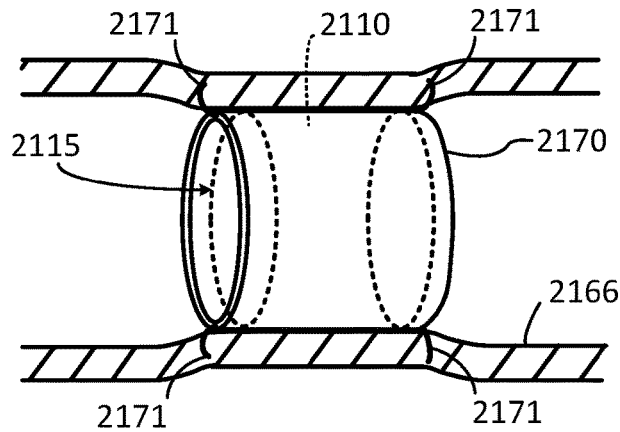

FIGS. 23A-C illustrate an embodiment of an implantable body 2170 within a vessel 2166. The implantable body 2170 can be implanted within the vessel 2166 by delivery from a catheter, such as in the manner of being expanded like the stent shown in FIG. 22A-C (however, the delivery is not so limited and delivery may alternately include conventional techniques such as those used for implantation of a graft, stent, valve, filter or similar element as are known in the art). The implantable body 2170 may take the form of a tube having a wall that defines an outer circumference and a lumen 2115. The lumen 2115 can help maintain flow within the vessel 2166 by allowing air or fluid (e.g., blood) to pass through the lumen 2115.

Anchor elements 2171 are provided to anchor the implantable body 2172 to the walls of the vessel 2166. The anchor elements 2171 may be metal hooks that are connected to the implantable body 2170 and that extend distally and/or proximally of the implantable body 2170 and laterally outward from the implantable body 2170 to engage, and possibly sink into, the walls of the vessel 2166 during implantation.

One or more radially adjustable structures 2110, of any type referenced herein, can be mounted on the implantable body 2170 in any manner referenced herein. The one or more radially adjustable structures 2110 can be caused to expand, which can expand the inner and/or outer diameters of the implantable body 2170 as shown in FIG. 23B. Such expansion may expand the inner diameter of the vessel 2166 as the implantable body 2170 presses up against the walls of the vessel 2166 as shown in FIG. 23B. At other times, the one or more radially adjustable structures 2110 can be caused to contract to contract the inner and/or outer diameters of the implantable body 2170 as shown in FIG. 23C. The contraction of the implantable body 2170 can cause the vessel 2166 to decrease in inner diameter as shown in FIG. 23C. Such expansion and contraction may therapeutically regulate flow within the vessel 2166 by narrowing and widening the vessel 2166. Additionally or alternatively, a nerve (e.g., renal or vagus) close to the vessel 2166 can measure tension within the vessel 2166 and relay such information to the central nervous system to regulate blood pressure or other physiological parameter. Expansion and/or contraction of the vessel 2166, as shown in FIGS. 23A-C, can cause the nerve to send signals to the central nervous system in response to the expansion and/or contraction. The central nervous system can then regulate the physiological parameter, such as blood pressure, in response to the expansion and/or contraction. The physiological parameter, such as blood pressure, can be controlled by the expansion and contraction of the implantable body 2170.

Figure 24:
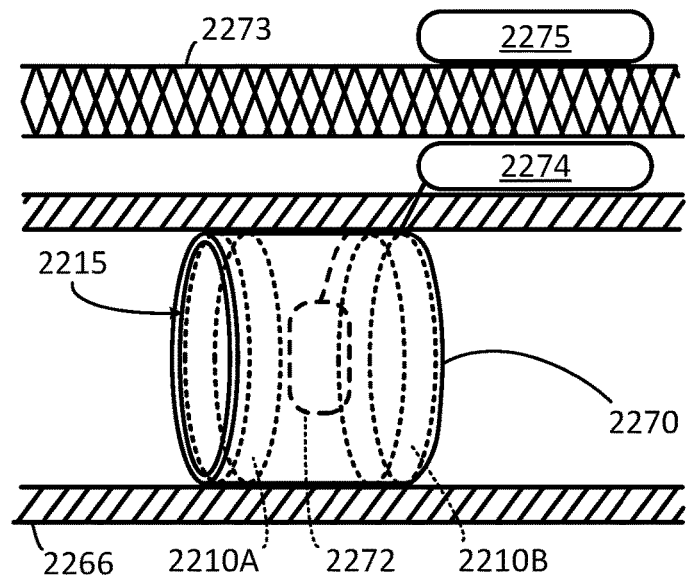
FIG. 24 is a schematic view of an implant configured to radially change.

FIG. 24 shows an implantable body 2270 that can be the same as the implantable body 1670 or otherwise have common features. The implantable body 2270 is implanted within a vessel 2266. Implantable body 2270 includes radially adjustable structures 2210A-B, which can be of any type referenced herein and can be embedded within the implantable body 2270 similarly to any embodiment referenced herein. While two radially adjustable structures 2210A-B are shown on distal and proximal sections of the implantable body 2270, just one, three, or another number of radially adjustable structures can instead be provided. The implantable body 2270 includes circuitry 2272. The circuitry 2272 can be embedded within the wall of the tubular implantable body 2270 similarly to how the radially adjustable structures 2210A-B, or other component referenced herein, can be embedded in a wall. Circuitry 2272 can include any of the components of the controllers 840, 1540. For example, circuitry 2272 can include a power source (e.g., a battery), an input (a pressure sensor, a biological parameter sensor such as a blood pressure sensor for closed loop operation, and/or telemetry for receiving a command), and/or a processor. The circuitry 2272 can output one or more signals to one or more motors within the radially adjustable structures 2210A-B to control expansion and contraction of the radially adjustable structures 2210A-B. In addition to a battery or as an alternative to a battery, an external transmitter 2275 can be provided outside of the skin 2273 to transcutaneously and wirelessly send command signals and/or energy (e.g., by inductive energy transfer) to the internal receiver 2274. The internal receiver 2274 can be connected by one or more wires to the circuitry 2272 to convey command signals and/or power.

While various embodiment show a radially adjustable structure embedded in a catheter or an implantable body, it is noted that any radially adjustable structure disclosed herein, such as in the form of an annular body, may be used in a patient's body while exposed such that it is not embedded in a catheter or an implantable body. In such a case, individual electrical components may be individually coated and insulted with a thin polymer layer. While the disclosed embodiments generally discloses medical devices that can expand and contract, in some embodiment a medical device may only be able to expand or contract but not both.

The present disclosure is made using various embodiments to highlights various inventive aspects. Modifications can be made to the embodiments presented herein without departing from the scope of the invention. As such, the scope of the invention is not limited to the embodiments disclosed herein.

I claim:

1. A method of in vivo motor operation for implant deployment in a patient, the method comprising:
   introducing a catheter body into the patient, the catheter body comprising one or more motors, wherein an implant is mounted in a radially compressed state on the catheter body, wherein the implant has a constant outer diameter in the radially compressed state;
   deploying the implant in vivo from the catheter body, the implant radially expanding during the deploying of the implant, the deploying of the implant driven by the one or more motors performing a plurality of actuation cycles while in vivo;
   wherein the one or more motors comprise a plurality of motors axially spaced from each other along the catheter body; and
   wherein deploying the implant comprises independently controlling the plurality of motors by actuating the plurality of motors different amounts such that the plurality of motors radially expand the implant to a radially expanded state in contact with anatomical structure surrounding the implant, the implant in the radially expanded state having a variable diameter along a length of the implant;
   withdrawing the catheter body including the motors from the patient while the implant remains in the radially expanded state with the variable diameter along the length of the implant and in contact with the anatomical structure within the patient.

2. The method of claim 1, wherein:
   the catheter body comprises a first outer diameter;
   the constant outer diameter of the implant comprises a second outer diameter; and
   deploying the implant from the catheter body comprises increasing the first outer diameter of the catheter body which causes the second outer diameter of the implant to increase, the increase in the first outer diameter driven by each motor of the plurality of motors performing the plurality of actuation cycles while in vivo.

3. The method of claim 1, wherein the implant comprises a proximal portion and a distal portion, the plurality of motors comprises a first motor and a second motor, the first motor located proximally along the catheter body relative to the second motor, and deploying the implant comprises:
   actuating the first motor through the plurality of actuation cycles to expand the proximal portion of the implant; and
   actuating the second motor through the plurality of actuation cycles to expand the distal portion of the implant, the first motor and the second motor being controlled such that the proximal portion is expanded to a different size than the distal portion.

4. The method of claim 1, wherein the implant comprises a stent.

5. The method of claim 1, further comprising controlling a controller in a handle connected to the catheter body, wherein controlling the controller comprises generating, in response to user input, one or more control signals that actuate the plurality of motors.

6. The method of claim 1, wherein the implant comprises a valve.

7. A method of in vivo motor operation for implant deployment in a patient, the method comprising:
   introducing a catheter body into the patient, the catheter body comprising one or more motors;
   deploying an implant in vivo from the catheter body, the implant radially expanding during the deploying of the implant, the deploying of the implant driven by the one or more motors performing a plurality of actuation cycles while in vivo;
   wherein the one or more motors comprise a plurality of motors axially spaced from each other along the catheter body; and
   wherein deploying the implant comprises independently controlling the plurality of motors by actuating the plurality of motors different amounts such that the plurality of motors radially expand the implant to a radially expanded state in contact with anatomical structure surrounding the implant, the implant in the radially expanded state having a variable diameter along a length of the implant;
   withdrawing the catheter body including the motors from the patient while the implant remains in the radially expanded state with the variable diameter along the length of the implant and in contact with the anatomical structure within the patient;
   wherein deploying the implant comprises radially expanding a plurality of radially adjustable structures of the catheter body via actuation of the plurality of motors to produce radial expansion of the implant;
   wherein the plurality of radially adjustable structures comprises a first radially adjustable structure and a second radially adjustable structure;
   wherein the implant comprises first and second portions disposed over the first and second radially adjustable structures, respectively;
   wherein when the catheter body is introduced into the patient, the first and second radially adjustable structures have first and second initial diameters, respectively, wherein the first and second initial diameters are the same; and
   wherein radially expanding the plurality of radially adjustable structures via actuation of the plurality of motors comprises radially expanding the first radially adjustable structure a first amount from the first initial diameter to a first expanded diameter to expand the first portion of the implant and radially expanding the second radially adjustable structure a second amount from the second initial diameter to a second expanded diameter, different than the first expanded diameter, to expand the second portion of the implant, such that the first and second portions of the implant have different diameters in the radially expanded state of the implant.

8. The method of claim 7, wherein the plurality of radially adjustable structures comprise a plurality of expandable rings.

9. A method of in vivo motor operation for implant deployment in a patient, the method comprising:
   introducing a catheter body into the patient, the catheter body comprising one or more motors;
   deploying an implant in vivo from the catheter body, the implant radially expanding during the deploying of the implant, the deploying of the implant driven by the one or more motors performing a plurality of actuation cycles while in vivo;
   withdrawing the catheter body including the one or more motors from the patient while the implant remains within the patient;
   wherein the one or more motors comprise a plurality of motors axially spaced from each other along the catheter body;
   wherein deploying the implant comprises independently controlling the plurality of motors such that the plurality of motors radially expand the implant to a radially expanded state having a variable diameter along a length of the implant;
   wherein deploying the implant comprises radially expanding a plurality of radially adjustable structures of the catheter body via actuation of the plurality of motors to produce radial expansion of the implant; and
   wherein the plurality of radially adjustable structures comprise a plurality of coiled strips, wherein each coiled strip has radially overlapping windings.

10. A method of in vivo motor operation for implant deployment in a patient, the method comprising:
    introducing an implant and a distal end section of a catheter body of an implant delivery device into the patient, wherein the implant delivery device comprises one or more motors mounted on one or more radially adjustable structures, wherein the one or more radially adjustable structures are disposed in one or more trenches formed in an outer surface of the distal end section of the catheter body, wherein the implant is in a radially compressed state and coupled to the distal end section of the catheter body; and
    actuating the one or more motors while the one or more motors are inside the patient, which causes the one or more radially adjustable structures to radially expand outside the one or more trenches to radially expand the implant from the radially compressed state to a radially expanded state inside the patient.

11. The method of claim 10, wherein the act of introducing comprises advancing the implant delivery device over a guide wire.

12. The method of claim 10, wherein the one or more motors comprise one or more piezoelectric motors.

13. The method of claim 10, wherein the implant delivery device comprises a handle comprising a controller including a user input and wherein actuating the one or more motors comprises actuating the controller via the user input to generate one or more control signals that actuate the one or more motors.

14. The method of claim 13, wherein the implant delivery device comprises one or more electrical conductors extending through the catheter body, wherein the one or more electrical conductors electrically connect the one or more motors to the controller.

15. The method of claim 10, wherein the implant is mounted in the radially compressed state around the distal end section of the catheter body and the one or more motors during the act of introducing.

16. The method of claim 10, wherein the one or more radially adjustable structures comprise one or more non-helical coiled strips, wherein each coiled strip has radially overlapping windings.

17. The method of claim 10, wherein the implant delivery device comprises a layer of compliant material covering the one or more radially adjustable structures and being attached to the outer surface of the catheter body at locations proximal and distal to the one or more radially adjustable structures, wherein the layer of compliant material radially expands relative to the catheter body when the one or more radially adjustable structures are radially expanded.

18. A method of in vivo motor operation for implant deployment in a patient, the method comprising:
    introducing an implant delivery device into the patient, wherein the implant delivery device comprises a handle comprising a controller including a user input, a catheter body extending from the handle, one or more electrostatic motors disposed along a distal end section of the catheter body, wherein an implant is coupled to the distal end section of the catheter body and is in a radially compressed state having a constant outer diameter;
    advancing the distal end section of the catheter body, the one or more motors, and the implant through a blood vessel of the patient; and
    while the one or more motors are inside the patient, actuating the controller via the user input to generate one or more control signals, wherein the one or more control signals actuate the one or more motors, which radially expand the implant from the radially compressed state to a radially expanded state inside the patient;
    wherein the one or more electrostatic motors comprise a plurality of electrostatic motors and the method further comprises independently actuating the plurality of electrostatic motors different amounts to radially expand the implant such that the diameter of the implant varies along its length in the radially expanded state.

19. The method of claim 18, wherein the implant comprises a valve.

20. The method of claim 18, wherein the plurality of electrostatic motors comprises first and second electrostatic motors and independently actuating the plurality of electrostatic motors comprises controlling the first electrostatic motor to undergo a first actuation cycle and controlling the second electrostatic motor to undergo a second actuation cycle that is different than the first actuation cycle.

* * * * *